US011238984B2

(12) United States Patent
Sternberg et al.

(10) Patent No.: US 11,238,984 B2
(45) Date of Patent: Feb. 1, 2022

(54) SYSTEMS AND METHODS FOR ENSURING QUALITY OF CARE SERVICES

(71) Applicant: Honor Technology, Inc., San Francisco, CA (US)

(72) Inventors: Seth J. Sternberg, San Francisco, CA (US); Sandy J. Ring, Portola Valley, CA (US); Cameron T. Ring, Portola Valley, CA (US); Monica Lo, San Francisco, CA (US)

(73) Assignee: Honor Technology, Inc., San Francisco, CA (US)

( * ) Notice: Subject to any disclaimer, the term of this patent is extended or adjusted under 35 U.S.C. 154(b) by 1103 days.

(21) Appl. No.: 15/136,858

(22) Filed: Apr. 22, 2016

(65) Prior Publication Data

US 2016/0314268 A1 Oct. 27, 2016

Related U.S. Application Data

(60) Provisional application No. 62/152,694, filed on Apr. 24, 2015.

(51) Int. Cl.
*G16H 40/20* (2018.01)
*G16H 40/67* (2018.01)
(Continued)

(52) U.S. Cl.
CPC ............ *G16H 40/67* (2018.01); *G06F 40/20* (2020.01); *G06Q 10/1095* (2013.01);
(Continued)

(58) Field of Classification Search
CPC ......... G06Q 50/24; G16H 10/20; G16H 40/20
See application file for complete search history.

(56) References Cited

U.S. PATENT DOCUMENTS 8,463,636 B2 6/2013 Ahsan et al.
8,635,215 B2 1/2014 Osterwalder et al.
(Continued)

FOREIGN PATENT DOCUMENTS

AU 2011235925 B2 4/2012
EP 2797056 A1 10/2014

OTHER PUBLICATIONS

USPTO, ISA/US, "Notification of Transmittal of the International Search Report and the Written Opinion of the International Searching Authority or the Declaration", dated Sep. 13, 2016, 11 pages.

*Primary Examiner* — Reginald R Reyes
(74) *Attorney, Agent, or Firm* — Kang S. Lim

(57) ABSTRACT

The present invention relates to systems and methods for ensuring quality of care services. After care is provided a confirmation is received. This may include a message regarding the care delivery from the provider. The confirmation and message may be conveyed to friends and family of the recipient. Location data from the provider, and feeds from the recipient's location are collected. Any lapses of care and emergencies based upon the location data and feeds are likewise identified. Identifying lapses of care and emergencies includes cross referencing length of time the provider spent at the recipient's location against tasks that were supposed to be performed at the location to determine if there is a discrepancy. Likewise, the time and location of the provider can be cross referenced against the confirmation to determine if there is a discrepancy. In some embodiments the feeds are also analyzed for trigger events.

18 Claims, 30 Drawing Sheets

(51) Int. Cl.
  *G06Q 50/10* (2012.01)
  *G06Q 50/22* (2018.01)
  *G06F 40/20* (2020.01)
  *G06Q 30/02* (2012.01)
  *G06Q 10/10* (2012.01)

(52) U.S. Cl.
  CPC ......... *G06Q 30/0282* (2013.01); *G06Q 50/10* (2013.01); *G06Q 50/22* (2013.01); *G16H 40/20* (2018.01); *Y02A 90/10* (2018.01)

(56) References Cited

U.S. PATENT DOCUMENTS

| | | |
|---|---|---|
| 8,805,894 B2 | 8/2014 | Valdiserri et al. |
| 2006/0257832 A1 | 11/2006 | Atkins et al. |
| 2011/0010200 A1 | 1/2011 | Firozvi et al. |
| 2012/0095779 A1* | 4/2012 | Wengrovitz ............ G16H 40/67 705/3 |
| 2012/0096005 A1* | 4/2012 | O'Connor .............. G16H 10/20 707/741 |
| 2013/0159008 A1* | 6/2013 | Mills ...................... G06Q 10/06 705/2 |
| 2013/0321637 A1* | 12/2013 | Frank .................... H04N 5/2257 348/152 |
| 2013/0335550 A1* | 12/2013 | Rochenski ............ G01M 3/002 348/82 |
| 2014/0156327 A1 | 6/2014 | Cai |
| 2016/0321506 A1* | 11/2016 | Fridental ............ G06K 9/00335 |

\* cited by examiner

☐ Activity
Lauren would like to walk at least 30 minutes during each appointment.

☐ Companionship
She loves to talk through her week and gossip about the neighbors. With six grandkids, she has plenty to talk about.

2100

TASKS: Edit

Housekeeping
William would like some help doing the laundry and cleaning the kitchen and the bathroom.

Transportation
Take William to the market on Tuesdays.

RECENT NOTES View All

Tuesday, March 24
The first appointment went well. We created a care plan and decided we would meet twice a week.

SCHEDULE: Edit

Tuesdays
3:00pm - 5:30am

Fridays
2:00pm to 4:00pm

1:05 PM Thursday, April 4

Thank you
for rating today's visit.

Touch the screen to see your photos

SYSTEMS AND METHODS FOR ENSURING QUALITY OF CARE SERVICES

CROSS REFERENCE TO RELATED APPLICATIONS

This application claims priority to provisional application No. 62/152,694, filed Apr. 24, 2015, of the same title, which is incorporated by reference herein for all purposes.

Further, this application is related to co-pending application Ser. No. 15/136,853, (Attorney Docket Number HON-1601-US) filed Apr. 22, 2016, entitled "System and Methods for Facilitating Remote Care Service", which is incorporated by reference herein for all purposes.

Additionally, this application is related to co-pending application Ser. No. 15/136,854, (Attorney Docket Number HON-1602-US) filed Apr. 22, 2016, entitled "System and Methods for Matching Providers and Recipients for Remote Care Services", which is incorporated by reference herein for all purposes.

Lastly, this application is related to co-pending application Ser. No. 15/136,856, (Attorney Docket Number HON-1603-US) filed Apr. 22, 2016, entitled "System and Methods for Providing Value Added Services", which is incorporated by reference herein for all purposes.

BACKGROUND

The present invention relates to systems and methods for facilitating remote care of individuals. Such systems and methods will increase the effectiveness of remote care, feelings of independence and security of care recipients, and connectivity and sense of wellbeing for family and friends of the care recipient. Moreover, such systems and methods will provide service providers of the care with streamlined scheduling and routing, to more effectively deliver their services.

In home care is typically divided into two subsets: medical in home care and non-medical care. Non-medical care typically includes activities such as feeding, grooming and washing, assistance with bathroom habits, as well as many household tasks (such as cleaning, laundry, collecting mail, etc.). This assistance is critical for many individuals. Without these in home care services the recipient would often be unable to live independently, and would be forced to move in with family, or be institutionalized within an appropriate care facility.

In home care services are most typically used by the elderly. However, recipients of in home care can vary widely, including the mentally or physically disabled, persons recovering from a trauma or surgery, recovering addicts, or other individuals with enhanced care needs. However, with the aging demographics in much of the developed world, the need for in home care for the elderly, in particular, is expected to increase significantly.

Currently, in home care is often provided through an individual agreement between the recipient (or friends and family of the recipient) and a caregiver directly, or through an agency. As friends and family may not be geographically close to the recipient, there are hurdles in securing adequate care, and moreover stress and concern that the care is being properly administered with compassion. For family located away from a care recipient, it may be very difficult to even find a suitable care provider, let alone properly manage the recipient's care needs. Using an agency alleviates the difficulties in finding a caregiver; however, agencies are loath to provide any direct contact between the care provider and the recipient's family for fear of losing business (via a direct relationship not involving the agency).

Moreover, the vast majority of care agencies are notoriously low tech, both in distributing their care providers, scheduling, matching care providers to recipients, and the like. Often scheduling the providers is done manually using a pen and paper. More sophisticated agencies may have rudimentary scheduling software, but this is the extent of agency sophistication currently.

It is therefore apparent that an urgent need exists for systems and methods to facilitate remote care of a recipient that addresses the multitude of deficiencies that currently plague agencies or individual arrangements. Such systems and methods result in more efficient routing of providers to recipients, better matching of recipients to their care providers, better quality of care, and peace of mind for family and friends of the care recipient. Additionally, such systems and methods may enable sophisticated value added services that improve the recipient's quality of life and safety.

SUMMARY

To achieve the foregoing and in accordance with the present invention, systems and methods for facilitating remote services is provided. In particular the systems and methods for remote services management are directed toward the insurance of service quality. This may have particular utility in the care of the elderly or others who may be physically or mentally limited in some capacity, as well as for other care needs such as babysitting, pet care, companionship services, and the like.

In some embodiments, after care is provided a confirmation is received. This may include a message regarding the care delivery from the provider. The confirmation and message may be conveyed to friends and family of the recipient. Location data from the provider, and feeds from the recipient's location are collected. The collected feeds include any of a video feed, an audio feed, an emergency signal, and a message from the provider collected when the provider is at the recipient's location. Any lapses of care and emergencies based upon the location data and feeds are likewise identified.

Identifying lapses of care and emergencies includes cross referencing length of time the provider spent at the recipient's location against tasks that were supposed to be performed at the location to determine if there is a discrepancy. Likewise, the time and location of the provider can be cross referenced against the confirmation to determine if there is a discrepancy.

In some embodiments the feeds are also analyzed for trigger events such as an audible call for help, unexpected movement, and lack of movement for a configured period of time. If a trigger event is detected then the feed may be routed to a human operator. A provider or emergency responder can then be dispatched, if directed by the human operator. The results of the dispatch can then be documented and reported out.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 13-25C are example screenshots for the various user interface screens provided to the provider and recipient, respectively, in accordance with some embodiment.

DETAILED DESCRIPTION

Figure 1:
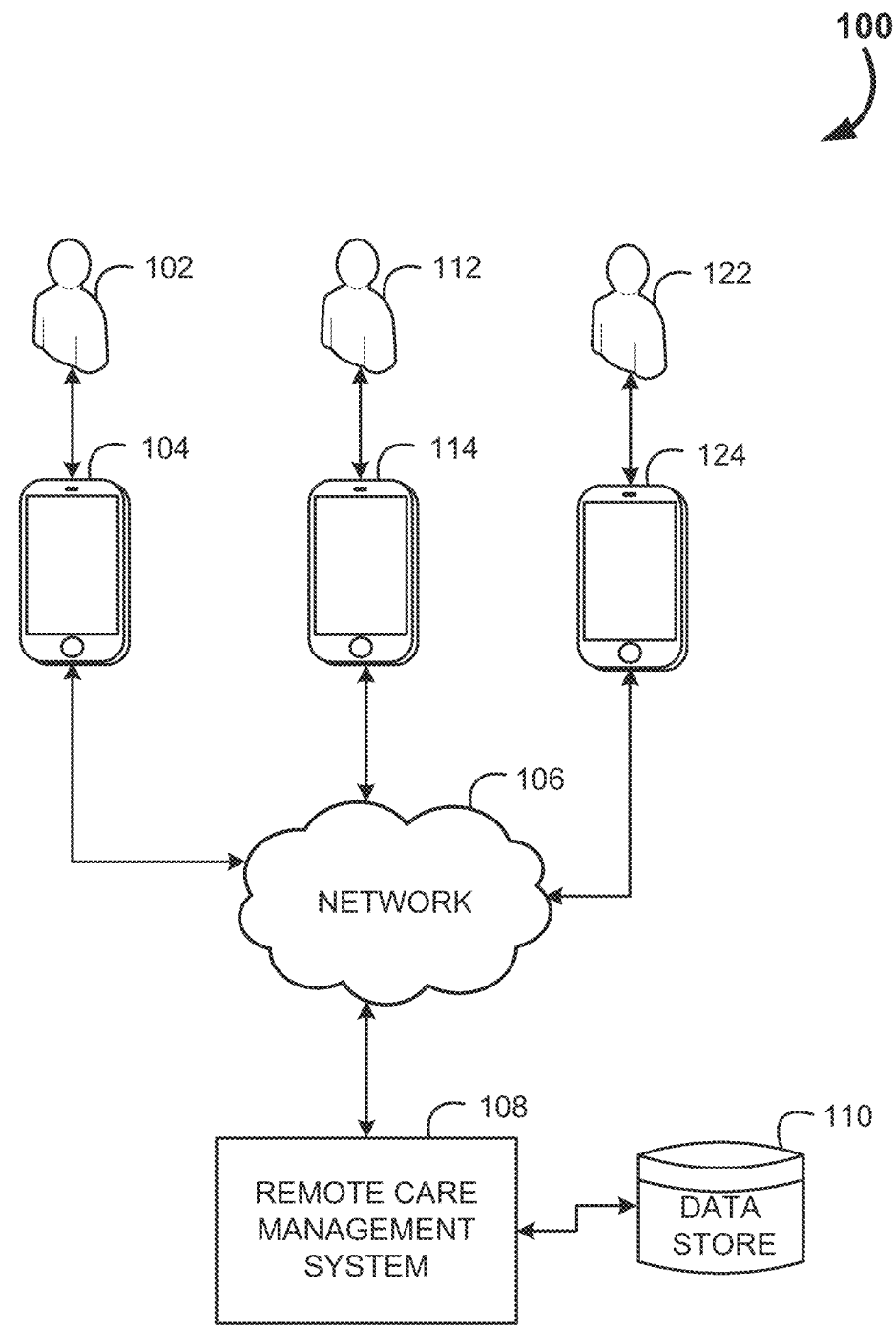
FIG. 1 is an example block diagram of a system for facilitating remote care, in accordance with some embodiment.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

The presently disclosed systems and methods are directed toward the management of remote care. Typically this care is non-medical care for assistance with activities needed for living independently. The term "remote" means that the assistance is delivered to the site of the recipient. In many cases, this includes assistance to the recipient's residence; however, the provided service may be delivered to any location where it is required (a grocery store for example).

Note, that throughout this disclosure, particular emphasis will be placed upon care services for activities such as feeding, grooming, assistance in adherence to prescription schedules, cleaning, and other household chores. However, the systems and methods contained herein are not required to be limited to such services. For example, such remote services may include companionship services, assistance with specific activities (such as physical therapy), or even childcare or other services.

Additionally, a number of terms are utilized throughout this disclosure that are intended to be read interchangeably. For example, the terms "provider", "service provider", "caregiver" and "care provider" are often utilized interchangeably to refer to the individual(s) who travel to the recipient and provide the required service. Likewise, "service", "assistance" and "care" are often employed to refer to what is being provided to the recipient. Moreover, "friends and family", "family" and "customer" may be used to refer to an interested third party to the recipient who is concerned with the recipient's wellbeing. This individual may even be the recipient's doctor, therapist, insurance company, or other non-familial individual. These third parties often are responsible for the payment of the care services; however this is not always required. Additionally, while "friends and family" are typically referred to as a single entity, this may include disparate groups that desired to have feedback regarding the recipient's care.

Note that the following disclosure includes a series of subsections. These subsections are not intended to limit the scope of the disclosure in any way, and are merely for the sake of clarity and ease of reading. As such, disclosure in one section may be equally applied to processes or descriptions of another section if and where applicable.

I. REMOTE CARE MANAGEMENT SYSTEM

To facilitate this discussion, FIG. 1 provides an example schematic block diagram for a system for facilitating remote care, shown generally at 100. Here the three main parties are illustrated: the service provider 102, the service recipient 112, and the recipient's friends and family 122. These entities all have access to a computing device 104, 114 and 124 respectively.

The device 104 employed by the provider 102 may be any computing device; however, ideally the device is mobile (while maintaining network connectivity) and includes a GPS. Smartphones provide a very convenient platform, often the device 104 may be a smartphone, smart watch, or similar device.

While a smartphone may also function as the recipient's 112 device 114, in some embodiments the recipient 112 is elderly, or has physical or mental limitations. For these recipients 112, it may be beneficial for the device 114 to be as user friendly as possible. Often large script, bright screen, touch capabilities, and ruggedness are important. A tablet, such as an iPad or similar device, may be well suited for the recipient's 112 device 114 as the screen size is larger than that of a smartphone. This allows for enlarged images, and has built in touch screens.

These tablets may be "locked" such that the recipient 112 only has access to a handful of options in order to simplify the interface. In some embodiments, the functionality enabled on a given device 114 may be dependent upon the recipient's 112 needs, and technical capability. For example, a recipient with dementia may require the device 114 to be very limited in its functionality: perhaps only providing basic reminders and information regarding the provider. A more mentally competent recipient, who is comfortable with technology, may have a device 114 that has far more expansive functionality, such as web-access, streaming media content, email access, or the like.

In some embodiments, it may even be desirable for the recipient's 112 device 114 to be a custom piece of machinery adapted for the rigors that a recipient may subject the device to. For example, in some embodiments, the device may be hardened against physical damage if the recipient has late stage Parkinson's and has difficulty manipulating the device without it being routinely dropped. Likewise, some devices 114 may benefit from being waterproof, having tactile or audio interfaces (for the visually impaired), having non-removable cords (rather than battery powered devices), or the like.

The device 124 utilized by the friends and family 122 of the recipient are generally much more varied. Typically these devices 124 are used for feedback communication, and as such any device with Internet connectivity will typically suffice.

Each of the devices may access a remote care management system 108 via a network 106. The network 106 most typically includes the Internet, but may also include other networks such as a corporate WAN, cellular network, or combination thereof, for example. The remote care management system 108 has access to a data store 110, which includes information of each of the relevant parties, including access permissions, profile information, locations, feedback, etc.

Note, while a single recipient 112, service provider 102 and family and friends 122 are illustrated in this example diagram, there are typically a very large number of these entities accessing the remote care management system 108. Often a single recipient 112 may have one or more providers 102 providing them assistance. Likewise, a given provider 102 typically cares for a plurality of recipients 112 over the course of a week. Further, as already mentioned, a single recipient 112 may also have no family or friends 122, or may have a very large number of individuals who may be classified as such.

Figure 2:
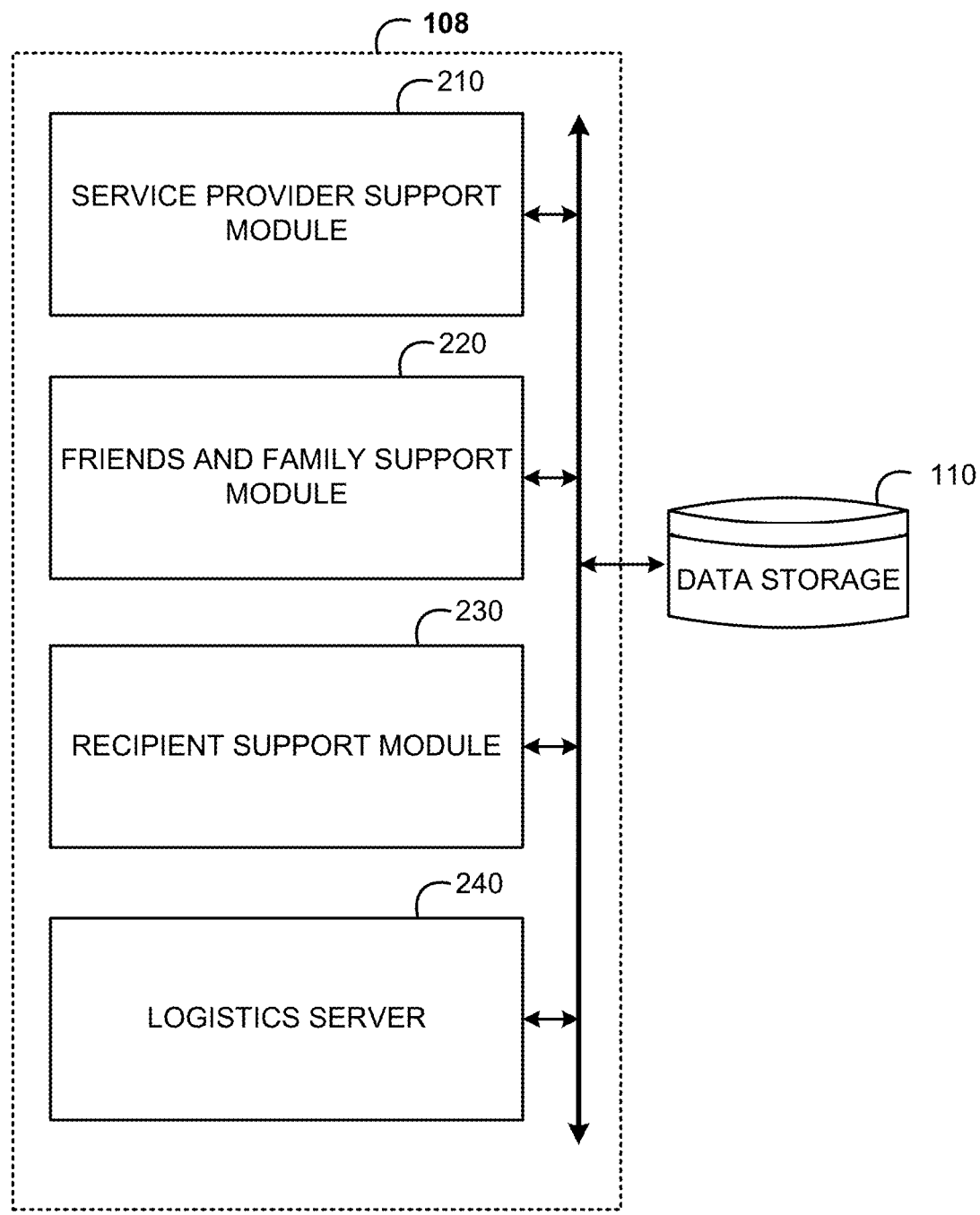
FIG. 2 is an example block diagram of the remote care management system, in accordance with some embodiment.

Moving to FIG. 2, a more detailed example block diagram of the remote care management system 108 is provided. The remote care management system 108 typically includes one or more servers that manage incoming traffic from the devices, and provides updates to the relevant devices to facilitate the delivery of care.

In particular, the remote care management system 108 has at least four logical subsystems that provide support to the provider, recipient and family/friends. Additionally, the remote care management system 108 performs a number of backend activities that require processing. In order to meet these demands, the remote care management system 108 includes a service provider support module 210, a friends and family support module 220, a recipient support module 230, and a logistics server 240. Each of these sub-systems shall be explored in greater detail in the following figures.

Figure 3:
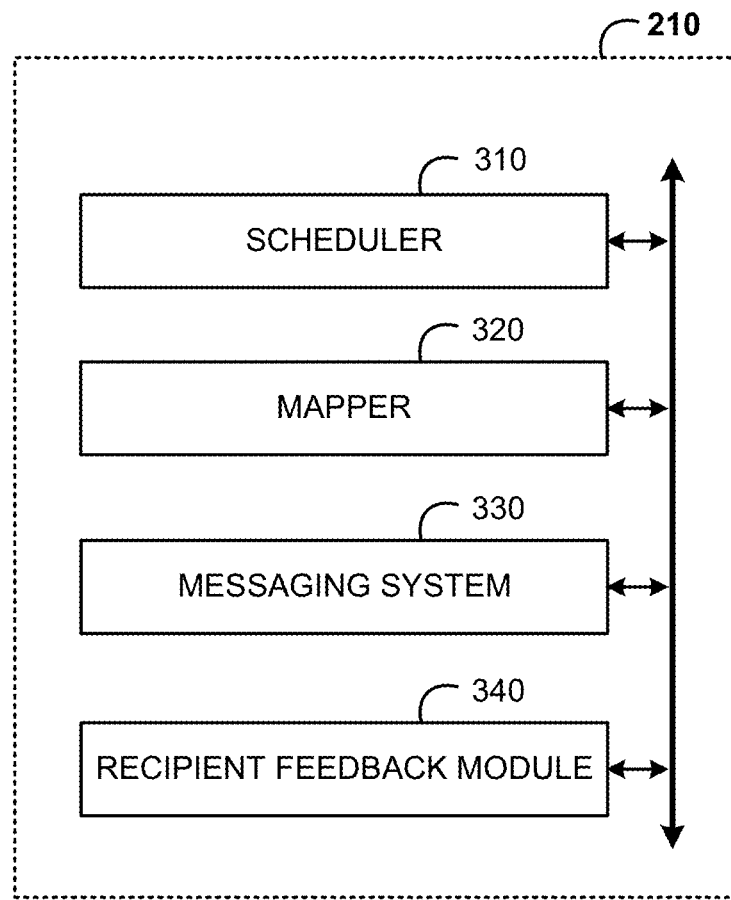
FIG. 3 is an example block diagram of the service provider support module of the remote care management system, in accordance with some embodiment.

FIG. 3 is the example block diagram of the service provider support module 210. This module includes a scheduler 310 which calculates where and when the provider has an appointment. In some embodiments, the scheduler utilized optimization processes based upon the provider's location to most efficiently deliver care to given recipients. In some advanced embodiments, the schedule may take into consideration travel times, traffic conditions, mode of transportation, etc. in order to dynamically update the provider's schedule. For example, if the provider is running long at an appointment due to an unforeseen complication, the scheduler may be configured to shift the entire schedule accordingly. The impacted recipients would be notified of the delay.

In the above example, if the delay became significant, the scheduler may be configured to determine which appointments are critical (as opposed to matters of convenience), and may ensure that all critical appointments are met in a timely manner. Less critical appointments may be rescheduled, or a substitute provider may be dynamically routed to the recipient based upon provider availability and locations.

The service provider support module 210 may also include a mapper 320 which utilizes the provider's location, and locations of the recipients' to provide directions and optimized routing to the provider's next appointment. Such features enable the provider to visualize their routes, avoid traffic congestion, and most efficiently get from one appointment location to the next.

The service provider support module 210 may also include a messaging system 330, which allows the provider 102 to directly communicate with the friends and family 122 of the recipient. This allows for 'on the fly' status updates to be communicated between the provider and the remote party.

Lastly, the service provider support module 210 may include a recipient feedback module 340. As will be discussed in greater detail below, the ability for providers and recipients to provide feedback regarding one another to the management system 108 enables optimization of provider-recipient pairings. This feedback may be kept secret, or the feedback may be may be provided in summary or aggregated form, in order to facilitate honest feedback.

Figure 4:
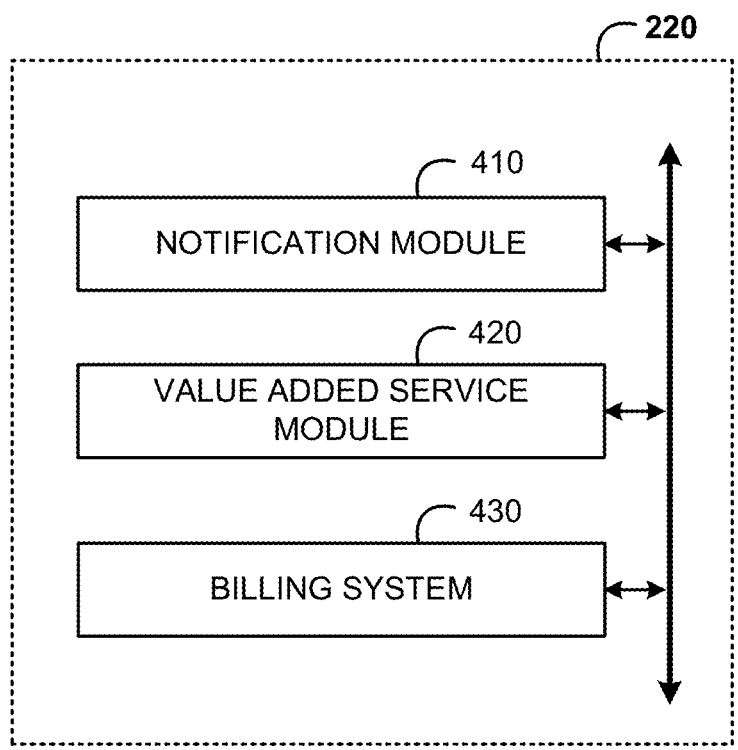
FIG. 4 is an example block diagram of the friends and family support module of the remote care management system, in accordance with some embodiment.

Moving on to FIG. 4, an example block diagram of the friends and family support module 220 is provided. The friends and family support module 220 consists of a notification module 410, a value added services module 420, and a billing system 430.

The notification module 410 pushes updates and notifications regarding the recipient 112 to the friends and family 122. These updates may include messages generated by the providers 102, and may further include reminders and status updates regarding service, billing cycles, etc.

The value added service module 420 provides offers for additional services or opportunities based upon analysis of the recipients 112 profile, wants and needs. Unlike traditional care agencies, the presently disclosed system benefits from transparency and the ability to leverage datasets to improve care of the recipient. A wealth of information is collected regarding the recipient, including an expansive profile which is populated upon signing up for the care services. This profile may include age, gender, weight, height, hobbies, previous professional experience, location, pets, physical and mental limitations, personal accomplishments, traditions, favorite holidays, favorite gift received, most treasured memory, favorite person, subjective "perfect day", what is valued most in a friend, etc. This profile may be compiled by the recipient herself, or by the friends and family of the recipient.

In addition to this exhaustive profile, over time the various providers 102 caring for the recipient 112 generate notes and updates regarding their interactions. In some embodiments, these notes and messages may be analyzed using natural language processing techniques to generate additional insights regarding the recipient's 112 preferences. For example, the provider may message the recipient's friends and family that she "really enjoyed our walk today." Another provider, on a different day may compose a note that indicates the recipient "enjoys talking about flowers, and particularly roses."

The value added service module 420 may perform optimizations of events and additional services based upon these collected insights and profiles. For example, if sufficient numbers of individuals receiving care in a shared geographic location share similar interests, the system may generate an offer to charter a trip to the botanical gardens. Recipients who have interest in walks, gardens, flowers, social activities, and who maintain the physical capability for such an activity, may be provided the offer via the value added service module 420. Such activities often are subject to additional fees, and as such the offer may first be provided to the friends and family 122 (assuming they are handling the care finances). After approval by the financially impacted entity, the offer may be forwarded to the recipient to see if there is interest. Approval or rejection of offers may be tracked to further refine value added services that are offered.

Value added services include a large suite of possible activities. They may include special events, such as attending a touring concert, or may be periodic "field trips" such as the botanical garden example above. They may also include free or low cost routine services, such as a reoccurring social get together with individuals with similar interests. In addition to events, the value added services may include other services aimed at increasing the recipient's security, health, etc. For example, if the provider notes that the recipient has trouble making doctor's appointments; the system may query the recipient's profile and determine a suitable transportation means, and offer up a service to ensure medical appointments are met. For example, if the recipient is relatively sound mentally and emotionally, a simple car service may be sufficient to ensure appointments are met. However, special accommodations may be required for a recipient in a wheelchair, or with dementia, for example. After the value added service is accepted, the necessary transportation is scheduled.

Another example of a value added service could include non-provider commercially available services. For example, the provider may note that the recipient is having difficulty caring for a pet, or maintaining basic maintenance on the home. This may translate into the system offering to arrange a dog walking service, or a handyman service. In some embodiments, along with the care providers, these additional service providers may be vetted in order to ensure that only trusted individuals are interacting with the recipient. Unfortunately, there is a propensity for service providers to take advantage of the elderly, or any other member of society which is marginalized. Often there is little recourse available. The value added services provided here minimize this risk by ensuring the service is actually required (via provider observation), and ensures that the services are delivered by accountable individuals who have a vested interest in treating their clients fairly (in order to remain a preferred vendor).

An additional value added service that the system may provide includes recipient monitoring services. For recipients with frail health, or a mental disability such as Alzheimer's, there may be a significant emotional toll placed on friends and family who are located possibly hundreds or thousands of miles away. It may be possible to introduce monitoring services that are automated that can address these concerns.

Monitoring services may include video and/or audio monitoring, as well as health statistics collection. For health data collection, the recipient's device may include a platform that simply collects basic health data in an automated fashion. For example, the device may include an optical transducer for collecting blood oxygenation and pulse data. A blood pressure cuff may also be included, in some embodiments, which allows the collection of blood pressure data by the system. The device may also be coupled to a wireless network along with peripheral devices, such as a scale, glucose monitors, pedometer, accelerometer, etc., for collecting additional information such as weight, activity level, and evidence of a fall or other sudden acceleration. Alternatively, such data may be input by someone providing care to the recipient.

With regards to video and/or audio monitoring, the level of monitoring would be balanced by the recipient's desires. On one extreme, the recipient's home may be equipped with video and audio monitoring that ensures the recipient is safe. Other intermediate monitoring may include motion sensors which are automatically monitored and provide alerts if the level of motion is below a given threshold. For example, if the recipient is relatively motionless in their bed overnight, this may be deemed acceptable by the system, but a relatively motionless recipient within a hallway for twenty minutes may indicate a fall or other accident which has rendered the recipient immobile. Such a motion sensing system may be coupled with a video system that only activates when a "problem" is detected. This would allow rapid and efficient detection of problems such as a fall.

A "problem" detected by the motion sensing system, with or without a video system, may instead route one of the recipient's providers to the home to provide a 'check-in'. These services help ensure the recipient's health, and provide peace of mind to friends and family.

Of course, there are so many permutations of such monitoring services that listing them all within this disclosure would become burdensome. For example, the recipient's device 114 may be centrally located and include a motion sensor or camera. Thus the monitoring is limited to a single room as opposed to an entire home. Alternatively, rather than sensors embedded within the home, the recipient may be required to provide "check ins" via their device 114 at periodic times during the day, and an in home visit by a care provider will occur if the recipient misses the check in.

Another security service may include the care providers having body cameras that allow the friends and family to see the care being provided as well as see the condition of the recipient and the home.

Moving on, the final aspect of the friends and family support module 220 is a billing system 430. The billing system enables the payment for the services of the providers, as well as value added services and the care management system as a whole. As noted previously, traditional care agencies limit contact between the providers and the friends and family of the recipient for many reasons, including fear that they will develop an arrangement where the provider is directly hired, which could eliminate the agency's role and lower costs to the customer. The current system does not harbor such concerns as the interface platform enables value independent from the mere identification of the providers.

Figure 5:
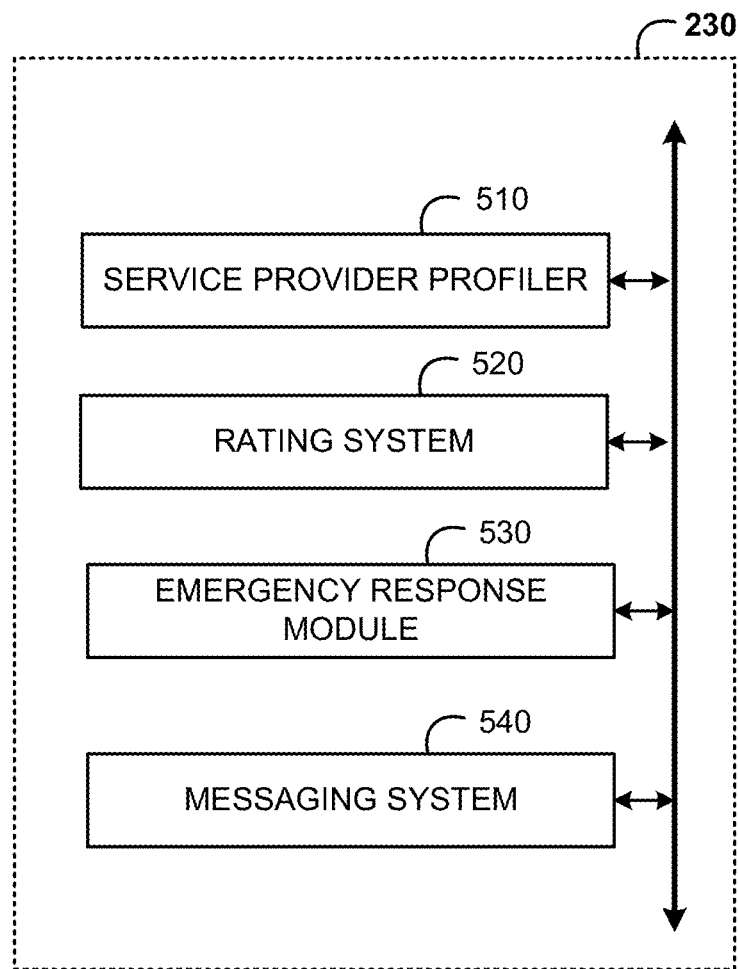
FIG. 5 is an example block diagram of the care recipient support module of the remote care management system, in accordance with some embodiment.

FIG. 5 is an example block diagram of the care recipient support module 230. A service provider profiler 510 provides the recipient an image of the provider, and indicates when the provider is going to arrive at the recipient's home. This eliminates surprises and unnecessary angst of the recipient by having someone dropping by unexpectedly.

Likewise, the recipient is asked to rate the provider via a rating system 520. As with provider ratings of the recipient, these ratings may be maintained in confidence in order to facilitate honest feedback, or may be provided on a summarized or aggregated basis. The rating system is utilized to hone provider-recipient matching, as well as provider eligibility decisions.

An emergency response module 530 may be made available on some recipient's devices where they are deemed mentally capable enough for such a feature. This enables the recipient to easily call for help in the care of an emergency by a simple selection of a "panic" style button on their device 114. Alternatively, the recipient may be provided a wearable interface or device that enables the recipient to rapidly request assistance when in an emergency situation.

Lastly, for some recipients, a messaging system 540 may enable communication directly with care providers, family and friends, medical personnel, mental health counselors, spiritual guidance counselors, and the like. The messaging system may also be employed to present the value added services to the recipient once they have been approved by the individual(s) controlling the system finances.

Figure 6:
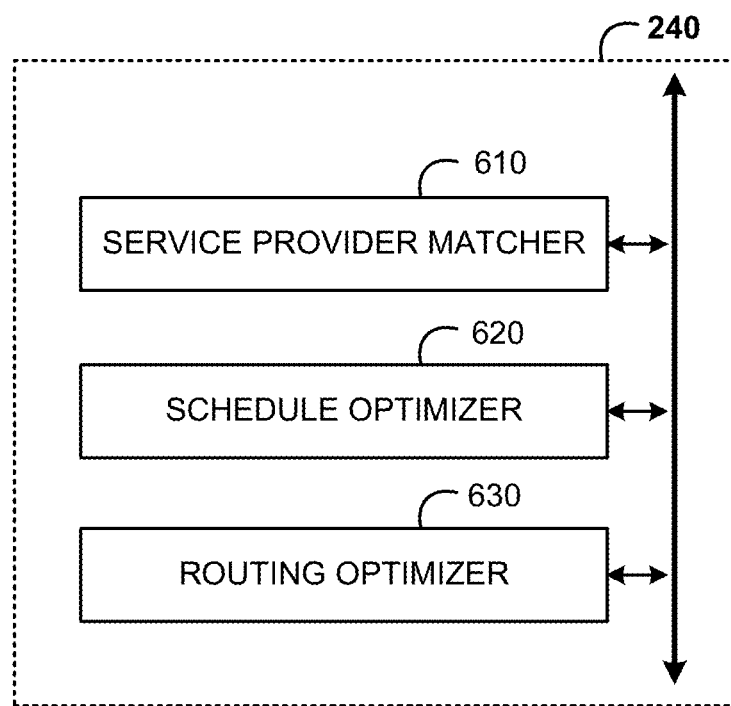
FIG. 6 is an example block diagram of the logistics server of the remote care management system, in accordance with some embodiment.

Moving on, FIG. 6 provides an example block diagram of the logistics server 240. The logistics server 240 performs the critical activities such as matching the provider to the recipients, via a service provider matcher 610. This matching process will be described in greater detail below, and utilize profile matching and optimizations based upon feedback to ensure the most successful recipient-provider matches.

A schedule optimizer 620 optimizes the schedules for the providers 102 based upon their location, the locations and needs of their recipients, and provider limitations. In concert, the routing optimizer 630 performs the routing of the provider to each recipient appointment. In some cases, the form of transportation utilized by the provider (car, bike, public transportation, etc.) may be taken into consideration for this routing. In yet other embodiments, the routing optimizer 630 can arrange for shared transport of providers and/or recipients to further increase efficiencies. For example, many recipients may already depend upon a bus service for the disabled in order to maintain their mobility. If these ride sharing services have dedicated route, providers may be able to leverage these existing infrastructures to get to their appointments.

Now that the systems employed for the management of remote care have been described in considerable detail, attention shall be redirected toward the processes employed to facilitate the efficiencies in the care.

II. METHODS FOR REMOTE CARE MANAGEMENT

The following figures and descriptions are but some exemplary embodiments for the methods of managing remote care. It should be realized that permutations and substitutions of the disclosed methods in order to improve performance of the care management is considered within the scope of this disclosure.

Figure 7:
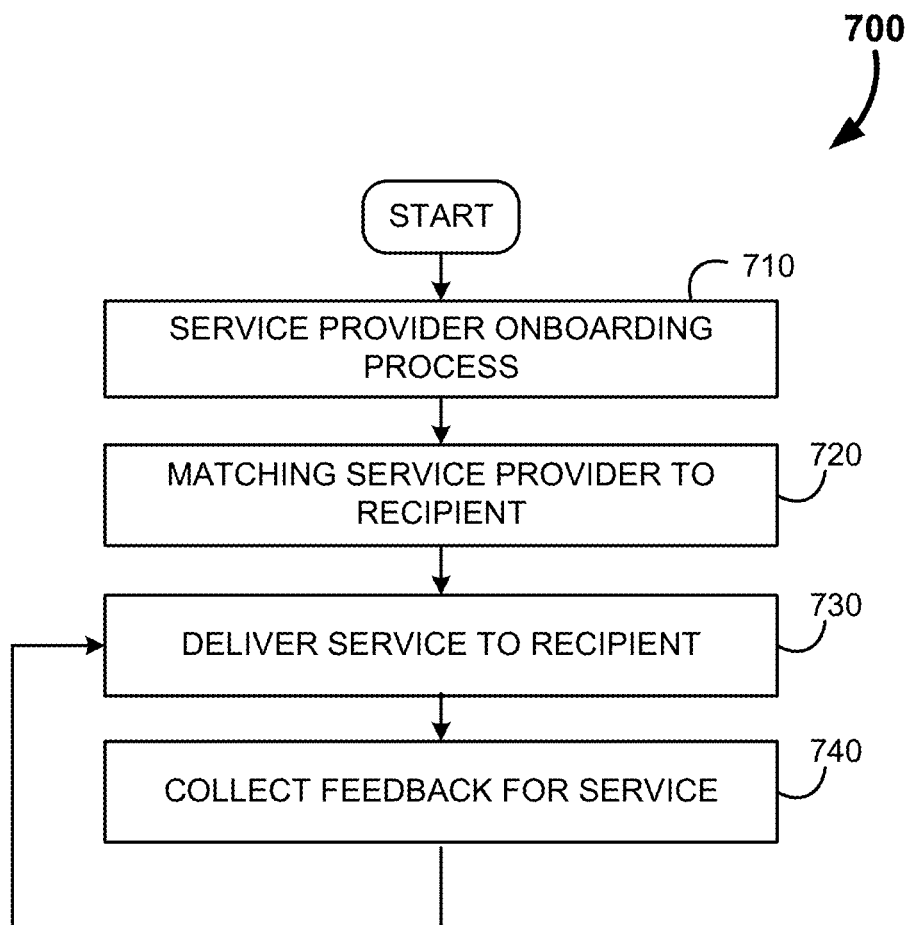
FIG. 7 is an example flow diagram for the process of delivering remote care, in accordance with some embodiment.
Figure 8:
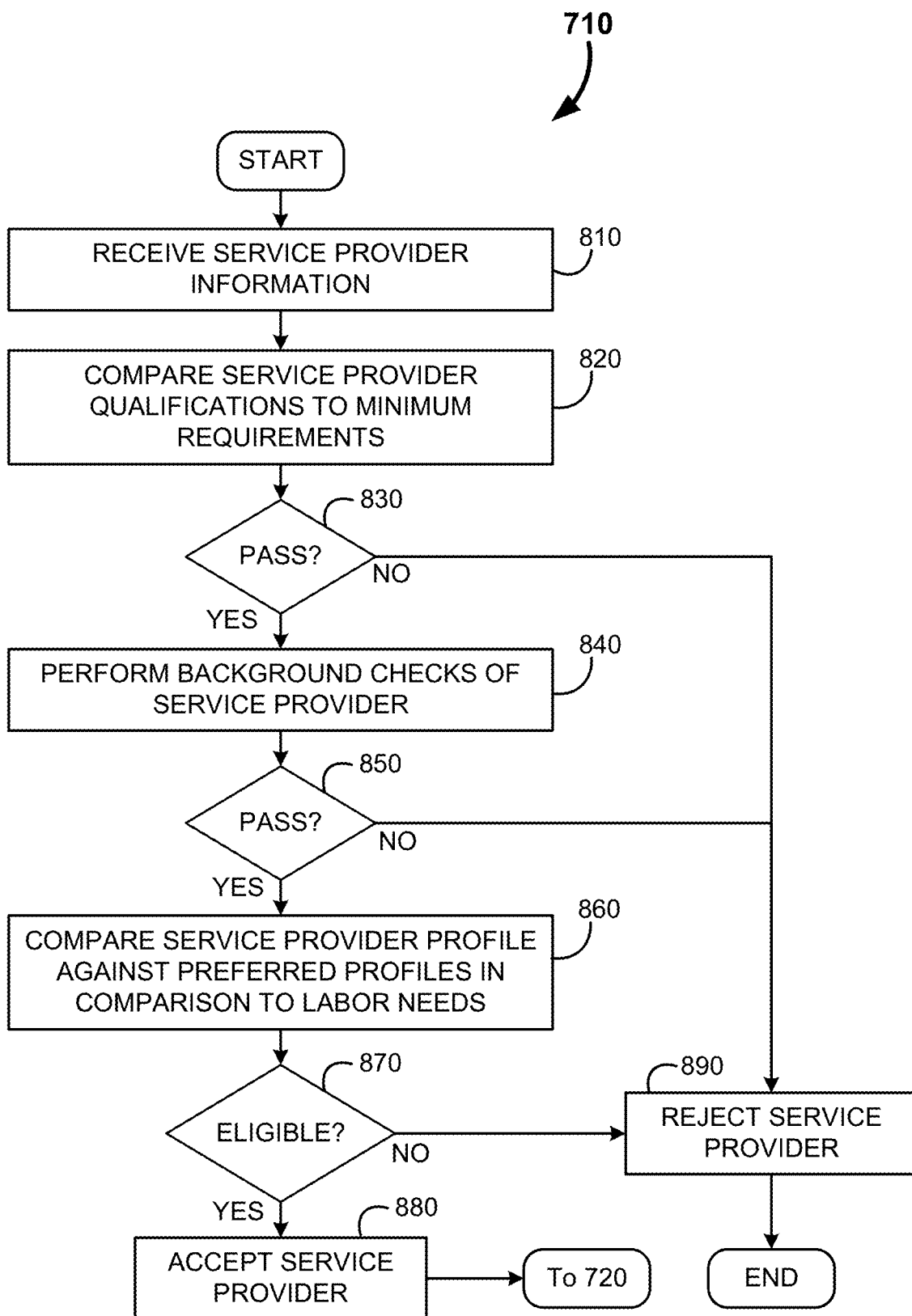
FIG. 8 is an example flow diagram for the sub-process of provider onboarding, in accordance with some embodiment.

FIG. 7 is an example flow diagram for the process of delivering remote care, shown generally at 700. Initially the service provider is on-boarded (at 710). FIG. 8 provides a more detailed flow diagram for the sub-process of provider onboarding, in accordance with some embodiment. Here the provider's information is received by the system (at 810). The provider information includes reference information, certifications, a personal profile, identification and previous work history. In some cases additional information may be required, such as health data, limitations, criminal records, etc.

The provider's qualifications are then compared to the minimum qualifications required for entry into the network (at 820). These qualifications may vary considerably based upon service provider availability, service needs, etc. For example, in some locations there may be a strong need for light duty providers that assist with feeding and basic grooming. The minimum requirements for such providers may be significantly lower than for providers in a location where the majority of the recipients are late stage dementia patients, for example.

A decision is made whether the provider meets these basic requirements (at 830). If not, then the provider is ineligible (at 890) to join the system as a provider. However, if the provider meets the basic requirements, the next stage is to perform a series of background checks (at 840). These background checks evaluate information regarding the provider's previous professional history, certifications, and the quality of the references provided about the applicant. Additionally, a criminal background check is performed, and in some cases a review of the applicant's social media accounts and credit scores may be required.

A provider has the unique privilege and responsibility of working very closely within the home of individuals who often are unable to protect themselves from abuse, theft or fraud. As such, the providers have to be very carefully screened. Again, if the applicant does not pass the background checks (at 850) they are rejected from eligibility (at 890).

However, if the applicant passes all background checks, the next stage is to compare the service provider's profile against preferred profiles (at 860). Since the presently disclosed systems and methods collect a relatively rich data set regarding providers' experience, certifications, professional information, and other background information, this data may be leveraged in order to generate profiles of providers that are most likely to meet the needs of the recipients. Thus, during the onboarding process for a new provider, the applicant's data may be compared against an in-demand provider profile. The degree of divergence between the applicant's information and the in-demand profile may be measured and compared against a threshold to determine if the applicant is eligible for the platform. The threshold may be dynamic, with a higher threshold to meet when there are plenty of providers already on-boarded, and a lower threshold when more providers are needed. In addition to the described vetting of a candidate, a series of in-person assessments may likewise be used to determine applicant eligibility.

If the profile of the applicant is too far below the threshold (at 870), the applicant is not admitted to the platform at that time (at 890). However, if the applicant passes each of these inquiries into their suitability, they are accepted as a provider (at 880). Acceptance includes ensuring they have access to the care management system 108 via an application running on their device 104. Additional information regarding their availability, transportation means, etc. may further be collected in order to facilitate the matching of the provider to recipients.

Figure 9:
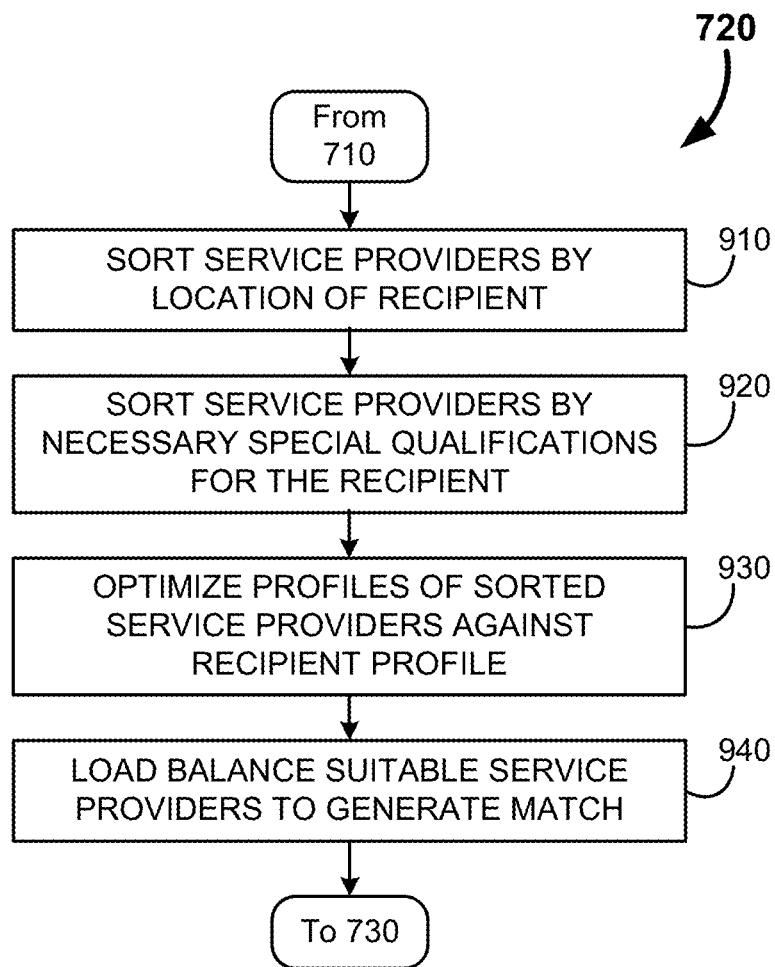
FIG. 9 is an example flow diagram for the sub-process of matching a provider to a recipient, in accordance with some embodiment.

Returning to FIG. 7, after provider on-boarding, the service provider is matched with a recipient (at 720), which is disclosed in considerable detail in FIG. 9. The matching step initially sorts providers by the location of the recipient (at 910). Immediately providers too far away from the recipient to be feasible may be discarded from a possible match.

Next, the providers that are close enough are then sorted by the necessary qualification for the given recipient (at 920). This sorting is entirely dependent upon the unique needs of the recipient. For example, if the recipient requires physical assistance with ambulation the provider must be able to provide it. Another example is where the recipient only speaks Spanish, and a multilingual provider is needed in order to effectively deliver care. Alternatively, a recipient may require a provider with specific skills, certification, etc.

The disclosed processes of narrowing a pool of providers by location and those who meet the special needs of the recipient is similar to what an agency already does. Typically these actions are performed manually, rather than via an automated process as disclosed herein. Where the present system excels over traditional approaches, is the suitable providers are then optimized for the recipients based upon their respective profiles (at 930). As already mentioned, a wealth of information is collected for both the recipient and the providers. Moreover, feedback is collected from both the providers and the recipients regarding their satisfaction working together. From this big data set, trends in profile compatibilities may be identified, and weights given to these correlations. Thus, when a new provider and recipient match is being considered, their profiles may be compared in light of these previously identified trends. Thus a provider may be selected that has the best "fit" to the recipient.

If there is more than one provider that is a suitable "fit" to the recipient, their respective schedules may be analyzed in order to load balance the providers (at 940). This ensures equitable distribution of work, and helps to avoid burnout. However, as can be appreciated, in alternate embodiments it may be beneficial to fill a provider's schedule completely before delegating work to another provider. Thus, based upon provider preferences, number of providers and market competitiveness a number of methodologies for workload balancing may be employed.

Alternatively, the system may present a number of suitable providers to the recipient and/or family, and allow them to select the provider. It may be possible that the providers bill as different levels as well, and these pricing differentials may be taken into consideration when selecting a provider.

An alternative to the sophisticated matching process disclosed above, is to enable a marketplace approach to provider-recipient matching. In such alternate embodiments, providers may be notified of a recipient that requires care. Details such as general location of care delivery, special needs, schedule of care required, and maybe even profile details, may also be made available to the provider. If the provider is interested, they may then apply to the recipient. The recipient and/or family members may then review the profiles of all interested providers in order to select a provider that they are most interested in.

While such a marketplace style matching process may forego profile matching, it allows the providers to also set fees for their services more dynamically. Thus, providers with more education/experience/credentials may be able to leverage their expertise in order to demand higher rates of pay. Indeed, even when the system matches providers with recipients independent from the marketplace disclosed here, various providers may command differing pay rates.

Additionally, hybrid approaches may be employed, where the location and needs of the recipient are considered, and a profile optimization is performed in order to render a "suitability index". This index may a simple scale, from 1-10 for example, which indicates whether the system believes the fit is good between the given provider and a recipient. This may be leveraged by providers when they decide whether to pursue a given position. Likewise, this index could be utilized by the recipient when making a selection between the interested providers.

Another hybrid approach is to identify all suitable providers for a given recipient, and present the opportunity to each provider. Suitability requires that the provider meets all the basic needs of the recipient, and services the geographic location in which the recipient resides. Once the providers are presented the opportunity, a subset will choose to 'apply' in a similar manner as described with the marketplace approach. However, rather than enabling the recipient's friends and family to ultimately decide which of the interested providers to use, in this approach, the system optimizes the fit between the recipient and all the interested providers. The best 'fit' provider is then awarded the care of the recipient.

Figure 10:
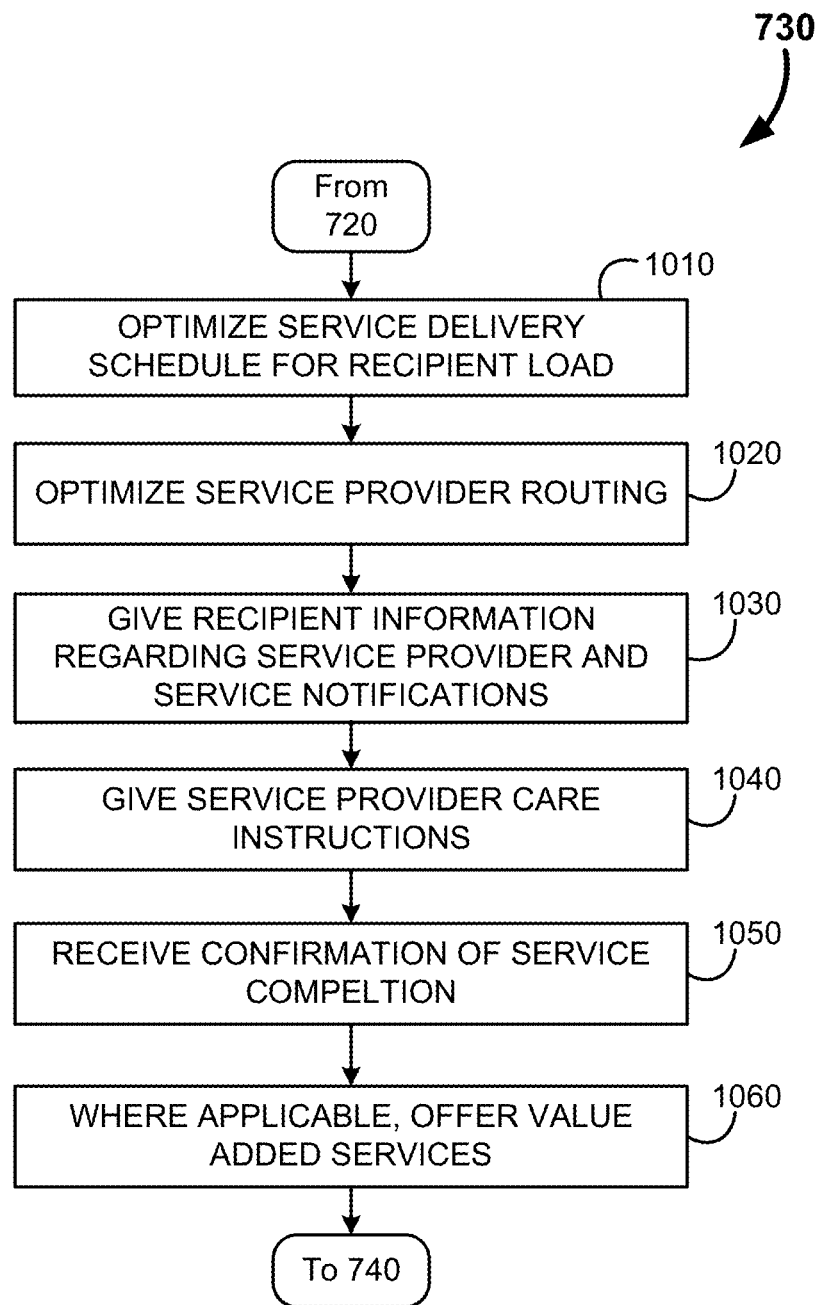
FIG. 10 is an example flow diagram for the sub-process of monitoring care delivery, in accordance with some embodiment.

Returning to FIG. 7, after matching the provider to the recipient, the service is delivered by the provider(at 730), which is described in greater detail at FIG. 10. Initially, the system optimizes the appointment schedule for the provider (at 1010). This process considers whether the provider has sufficient bandwidth in order to service each recipient. Many recipients may require care once or more times a day. However, some recipient may require fewer visits, and the scheduling process ensures that there is no overlap between the various recipients for a single provider. The scheduling process also takes into account the needs and preferences of the recipients, as well as location of recipients.

For example, one recipient may require help getting out of bed, and is scheduled first thing in the morning. The next appointment may be scheduled for a close location in order to minimize commuting burdens (and maximize time spent with recipients). The third appointment may be scheduled with a recipient requiring assistance with feeding, followed by another recipient at a close location for general help grooming. Then the provider may have to return to assist with feeding again.

Lastly, the scheduling optimization may learn from provider performance, and adapt as needed. For example, if the provider is routinely late between the third and fourth appointment, the scheduler may push back the fourth appointment in order to give the provider more leeway in getting to the appointment on time.

The next step is to provide optimal routing for the provider between the various appointments (at 1020). As the provider's device 104 includes GPS functionality, and mapping programs are readily available, it is a relatively trivial task to ensure the provider is routed most effectively between appointments. However, as previously mentioned, some embodiments of the present system may be further enabled to provide optimal routing based upon provider transportation preferences, or even match the provider with private shared transport.

The recipient is given information regarding the appointment on their device 114, including information on the provider (at 1030). As previously mentioned, this information may include an image of the provider, the provider's name, and the time of the appointment. This information ensures that the recipient is prepared to have the appointment, and reduces stress associated with having someone entering the home of the recipient.

Likewise, the provider is given information regarding the recipient (at 1040), including care instructions and access to the recipient's profile. Additionally, provider notes from previous appointments may be displayed to remind the provider of anything important. In some embodiments, it may even be possible for notes of other providers that are helping to care for the recipient to be displayed.

For example, assume the recipient has dementia and often behaves erratically. This individual may have multiple care providers. In the morning, the recipient refuses to eat, and is generally obstinate. The first care provider may leave a note for the next care providers cautioning them of the mood of the recipient, and indicating that feeding should be a priority due to the missed meal. This enables a greater degree of coordinated care than previously possible.

The provider arrives at the location of the recipient (typically the recipient's residence) and delivers the indicated care. The provider sends a confirmation to the care management system that the service has been rendered (at 1050). This confirmation is important to ensure the recipient is getting the needed care, for billing purposes, and it enables the friends and family of the recipient to check-in that the care has been provided.

Figure 11:
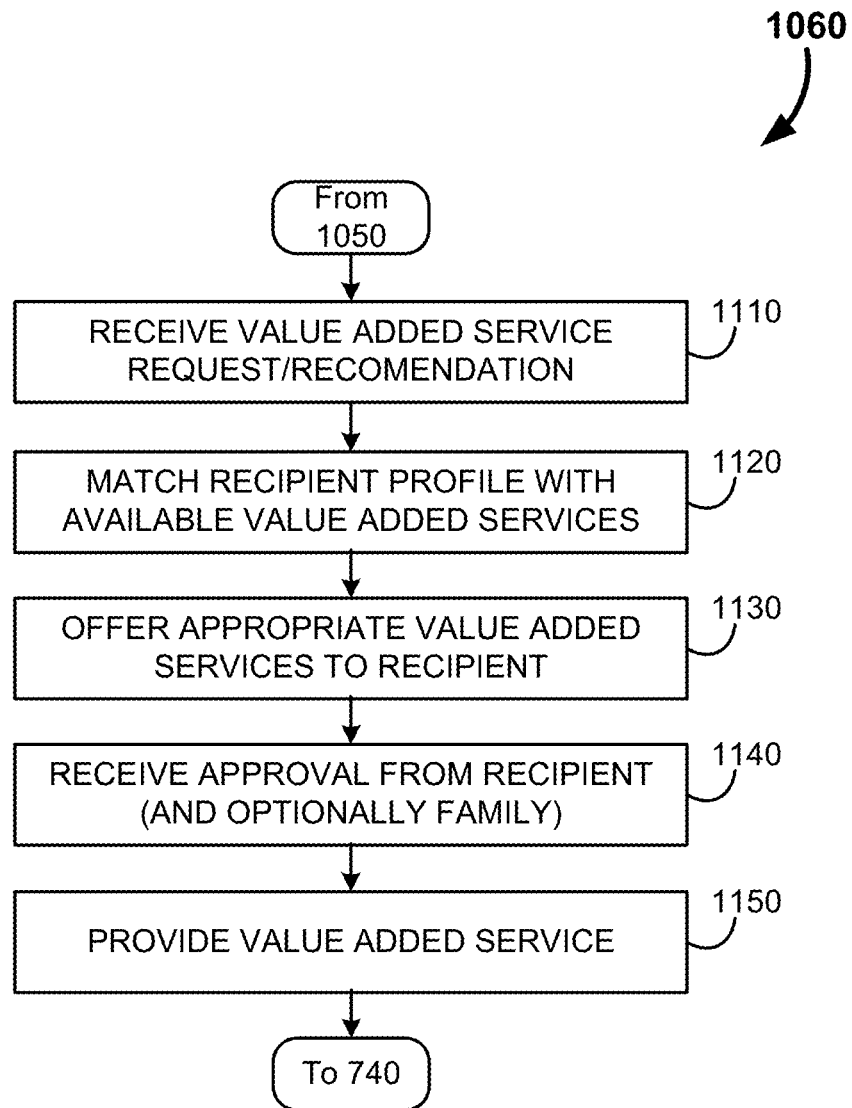
FIG. 11 is an example flow diagram for the sub-process of offering value add services, in accordance with some embodiment.

Lastly, when applicable, value added services may be offered (at 1060). The offering of these value added services is described in more detail at FIG. 11, where the system first receives a request or recommendation for a value added service (at 1110). This may be prompted by the availability of a new service (for example an event that is coming to town), a recommendation by the provider (for example, a message indicating the screen needs repair, or that the recipient could use a social outing), from the friends/family (for example, to celebrate a birthday a friend requests the recipient be given a special trip out), or even initiated by the recipient herself. In some cases, the recipient's device 104 may have a catalog of available value added services that may be browsed by the recipient. When the recipient finds something they are interested in, they may initiate a request for additional information (an possibly approval from the financial decision maker).

Once the request for a value added service is made, the system may match the recipient profile with the available value added services to determine a best fit (at 1120). For example, with regard to the request to repair the broken screen, a list of the handymen that have been vetted may be compared against the recipient's location in order to identify someone who would be able to promptly repair the screen. Likewise, for a request of a social engagement, the system may review upcoming events against the recipient's interests in order to find an event that they would enjoy, and have the physical ability to attend.

The next step is to offer the value added services to the recipient (at 1130) to see if they have interest in the service. If so, the next requirement is to ensure that appropriate approvals are secured (at 1140). For a mentally competent recipient with control over their finances, the recipient may be entirely capable of providing the required approval. However, in circumstances where finances are being controlled by friends or family, which is often the case when the recipient's mental capacity is diminished, the approval is sought from the appropriate individual.

After approval has been secured, the value added service may be provided (at 1150). The intention of these services is to make the process easy for the recipient. As such, the system may attempt to coordinate a visit from the handyman to repair the screen with an already scheduled appointment from the care provider. This enables the provider to be present to answer questions, provide access where needed, and alleviate any stress on the recipient. Likewise, the system may be adapted to handle logistics, such as meals, chaperones, transportation, etc. for any value added events.

Figure 12:
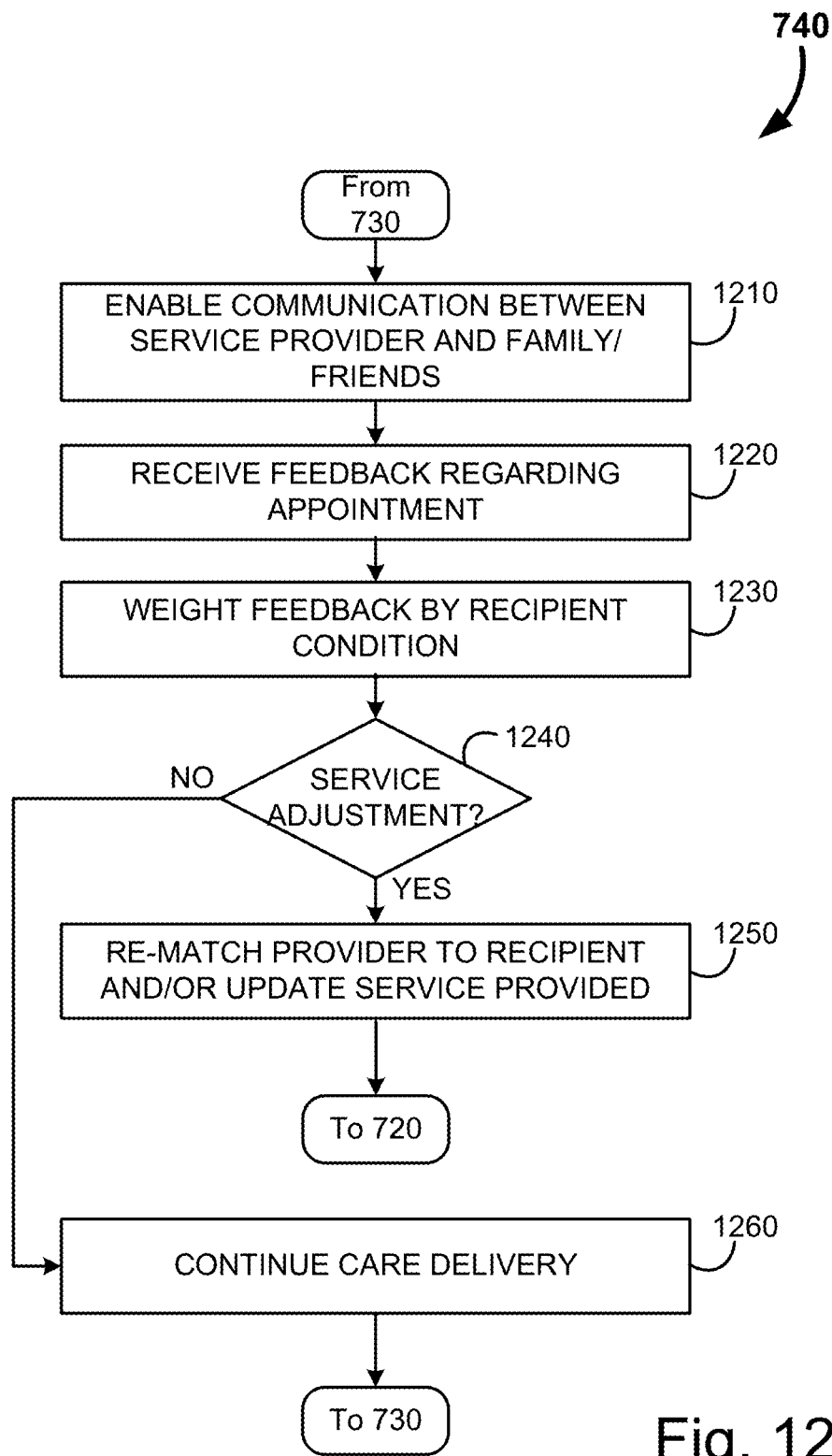
FIG. 12 is an example flow diagram for the sub-process of feedback collection, in accordance with some embodiment.

Returning to FIG. 7, after all services have been provided by the provider, feedback is sought (at 740) in order to improve the matching of providers and recipients, and to identify problems. FIG. 12 provides additional details regarding this sub-process of feedback collection, in accordance with some embodiment.

As previously mentioned, one of the unique advantages of the disclosed system is the level of transparency afforded providers to the friends and family of the recipient. To this end, communication is enabled between them (at 1210) through the care management system. The provider may send messages with updates to the friends and family. Likewise, in some embodiments, this messaging capability may be bidirectional.

In addition to this messaging, confidential feedback may be collected from the provider and the recipient (at 1220). This feedback may be utilized to refine the services between the provider and recipient, and further may be employed to help optimize future matching between other recipients and providers. Likewise, the rating of the provider may be employed, as previously discussed, to identify attributes of providers that are in high-demand. Note that while the feedback is helpful, it may be necessary to normalize any feedback provided by a recipient (at 1230) based upon the potential reliability of the rating taking into account various factors, which could include the rater's historical ratings, length of time on the platform, or specific individual attributes.

If the feedback collected indicates that an adjustment is needed in the service being delivered (at 1240), then proper adjustment may be undertaken. This typically may include altering the care being given, or may include re-matching a provider to the recipient (at 1250). However, in the case where the feedback indicates that there isn't a need for an adjustment, then care can be continued without any changes (at 1260).

III. EXAMPLES

Now that the systems and methods for the management of remote care has been described in considerable detail, attention will be turned to various examples of embodiments of the system being employed on one or more devices. To facilitate this discussion, FIGS. 13-25C are example screenshots for the various user interface screens provided to the provider and recipient, respectively. It should be noted that these screenshots are provided by way of example only, and are intended to clarify without unduly limiting the scope of the disclosure.

Figure 13:
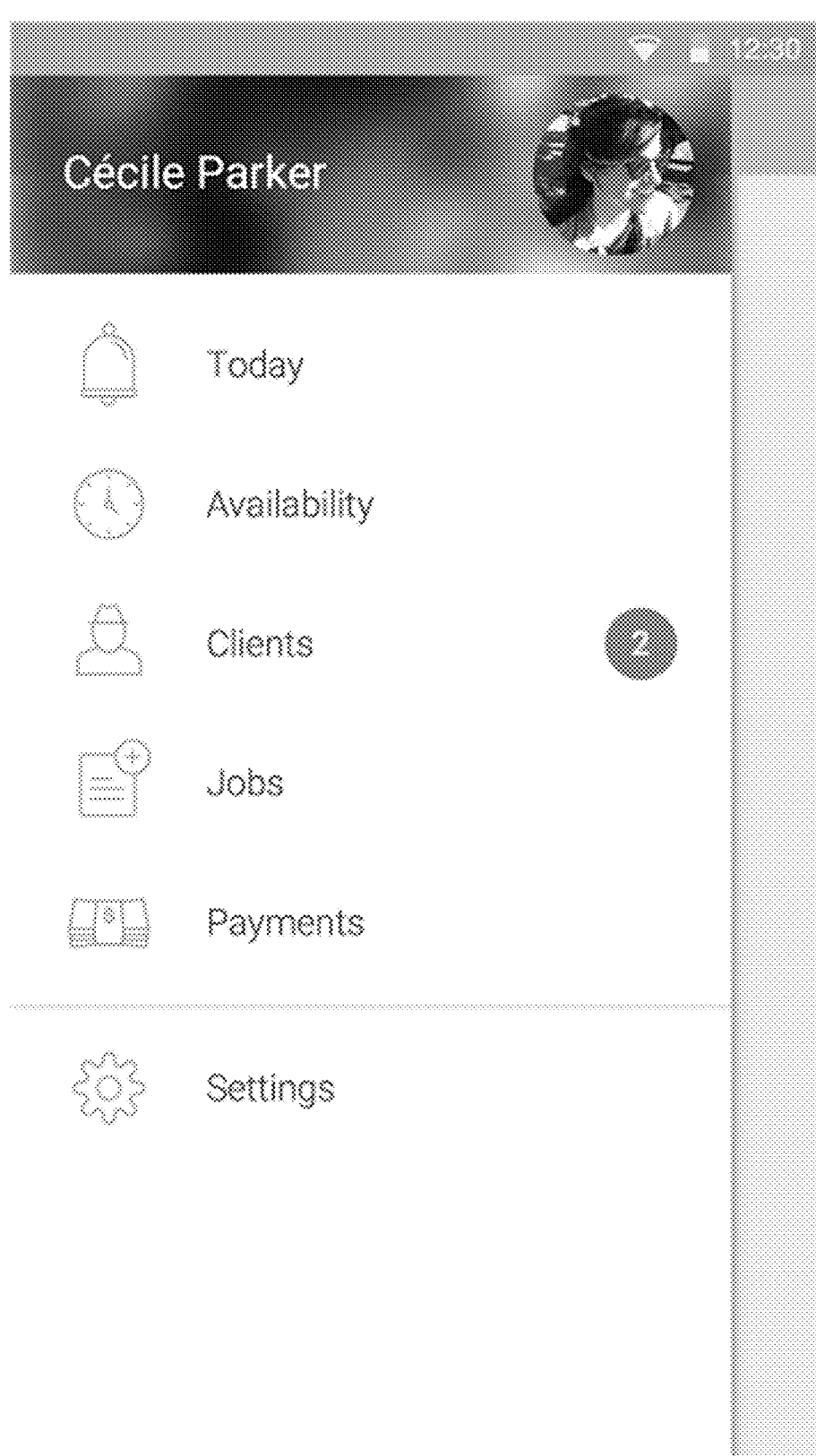

FIG. 13 provides a home screen that may be displayed on a provider's smartphone, or other mobile device, shown generally at 1300. Here, the home screen shows the provider's name and profile image at the heading, and includes a series of navigation menus that may be selected. In particular, the provider is given tools, availability, clients, jobs, payments and settings. A number of navigation menus will be explored in more detail in following screenshot figures.

The settings tool allows the provider to configure their display settings, login credentials (password and username), contact information, credentials, service area, etc. The availability menu allows the provider to select days and times when they are available to take jobs. This availability information may be employed during the scheduling process performed by the system. The payments menu may allow the provider to coordinate the payments made for the services that they provided.

Figure 14A:
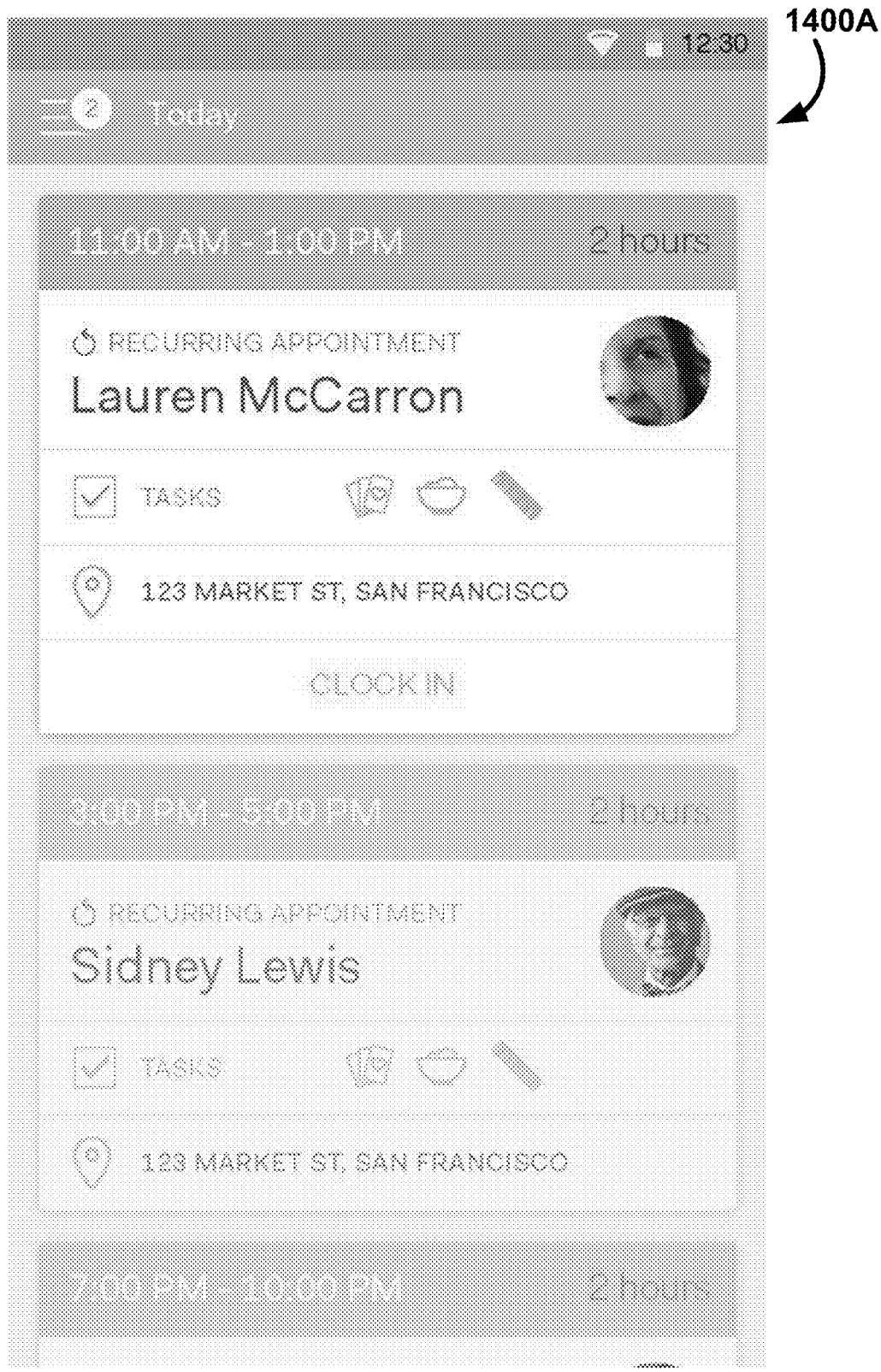
Figure 14B:
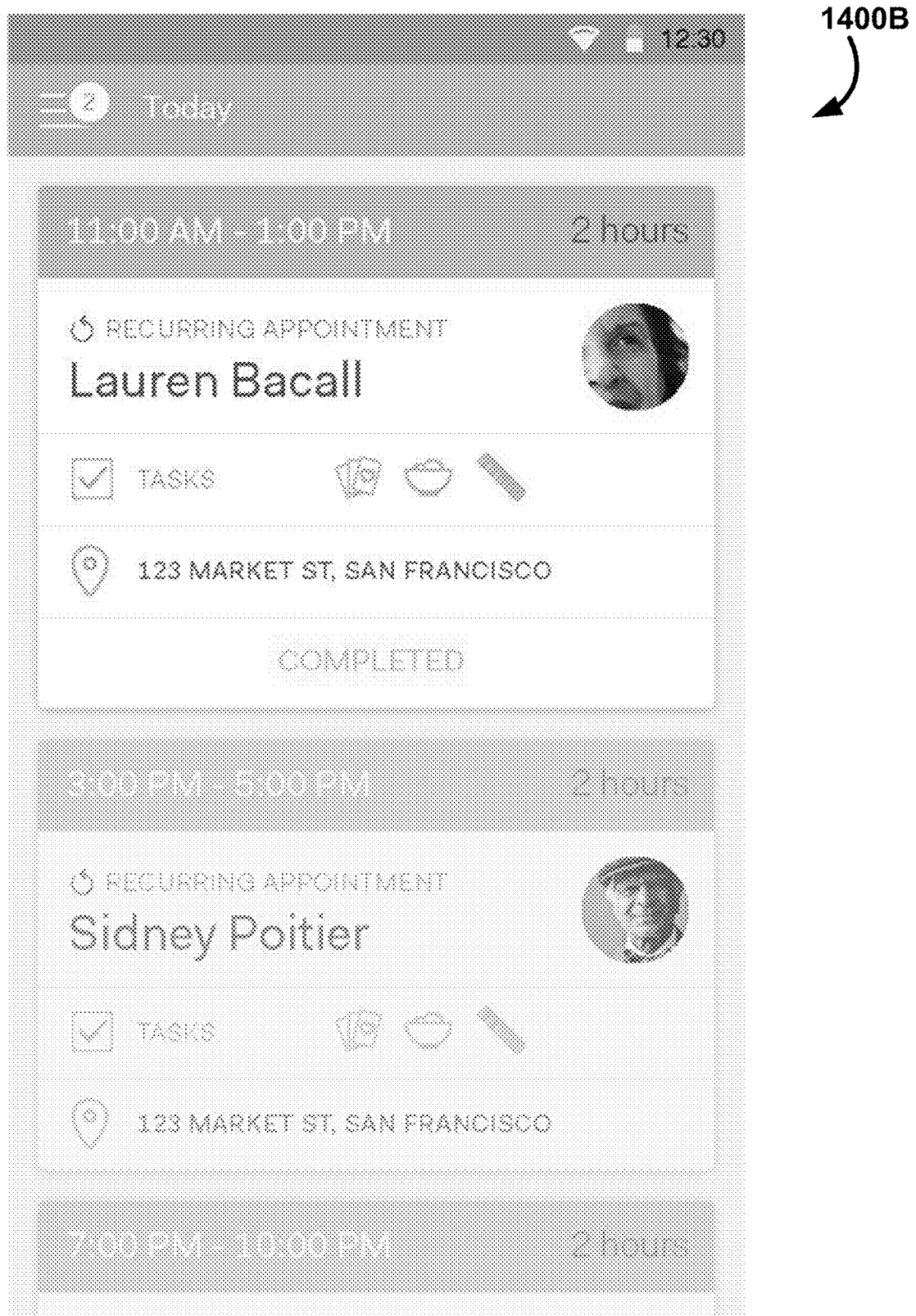

Moving on to FIG. 14A, the 'today' menu screenshot is illustrated for this example, shown generally at 1400A. Here the various appointments are shown to the provider, including the time of the appointment, duration of the appointment, type of appointment, who the appointment is with, what tasks are to be performed at the appointment, location, and the ability to clock in at the appointment once they arrive. In contrast, FIG. 14B shown a screenshot of the same 'today' menu example once the provider has clocked-in at the appointment, shown generally at 1400B. Now the provider is able to indicate that the appointment has been 'completed' once all tasks have been performed.

In some embodiments, the address may be selected by the provider in order to redirect to the routing system, which as previously discussed optimizes the provider's routing between appointments. Likewise, in some embodiments, the tasks illustrated may be selected to expand from the shortcut icons illustrated, to a full-blown explanation of the tasks to be performed, including special instructions.

Figure 15:
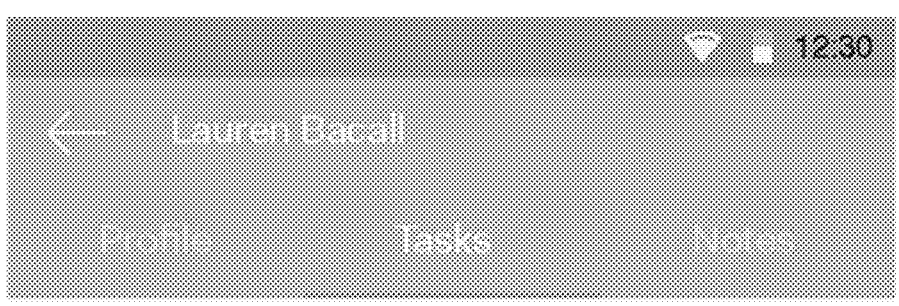
Figure 15:
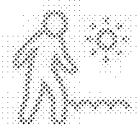
Figure 15:
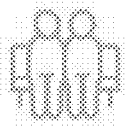
Figure 15:
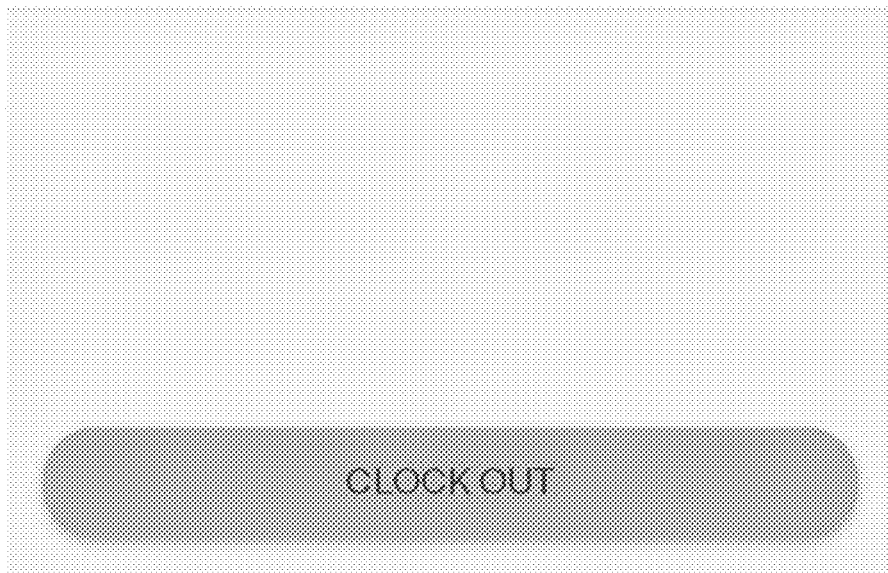

Additionally, the recipient's name or image may be selected, in some embodiments, in order to pull up the profile, tasks and notes for the given recipient. FIG. 15 provides an example screenshot of this menu where tasks have been selected for the initial appointment, shown generally at 1500. The activity is provided, including some details regarding the activity. For example, this recipient wants a minimum of 30 minutes of walking per appointment, and companionship. Details of what the recipient enjoys, topics of interest, etc. are likewise provided. These fields may be modified by the providers for their future reference, and may even be shared to other providers of a given recipient.

Figure 16A:
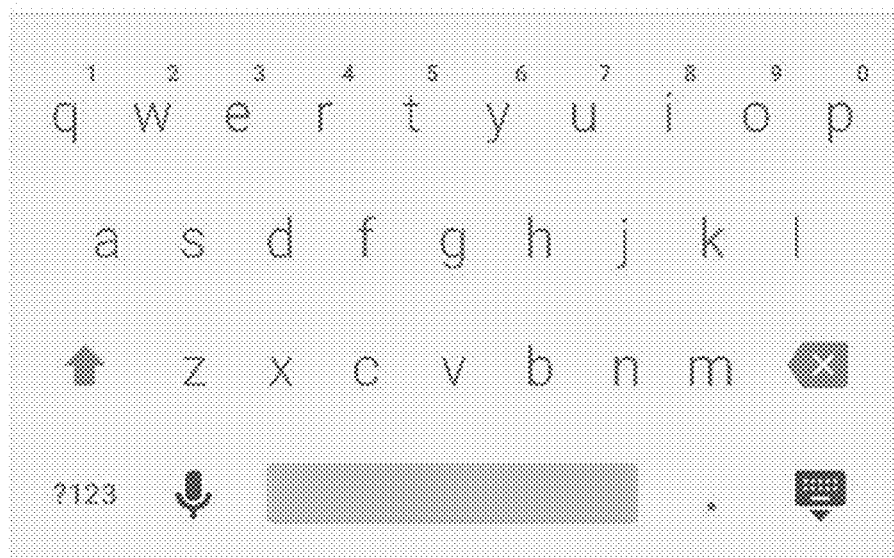
Figure 16B:
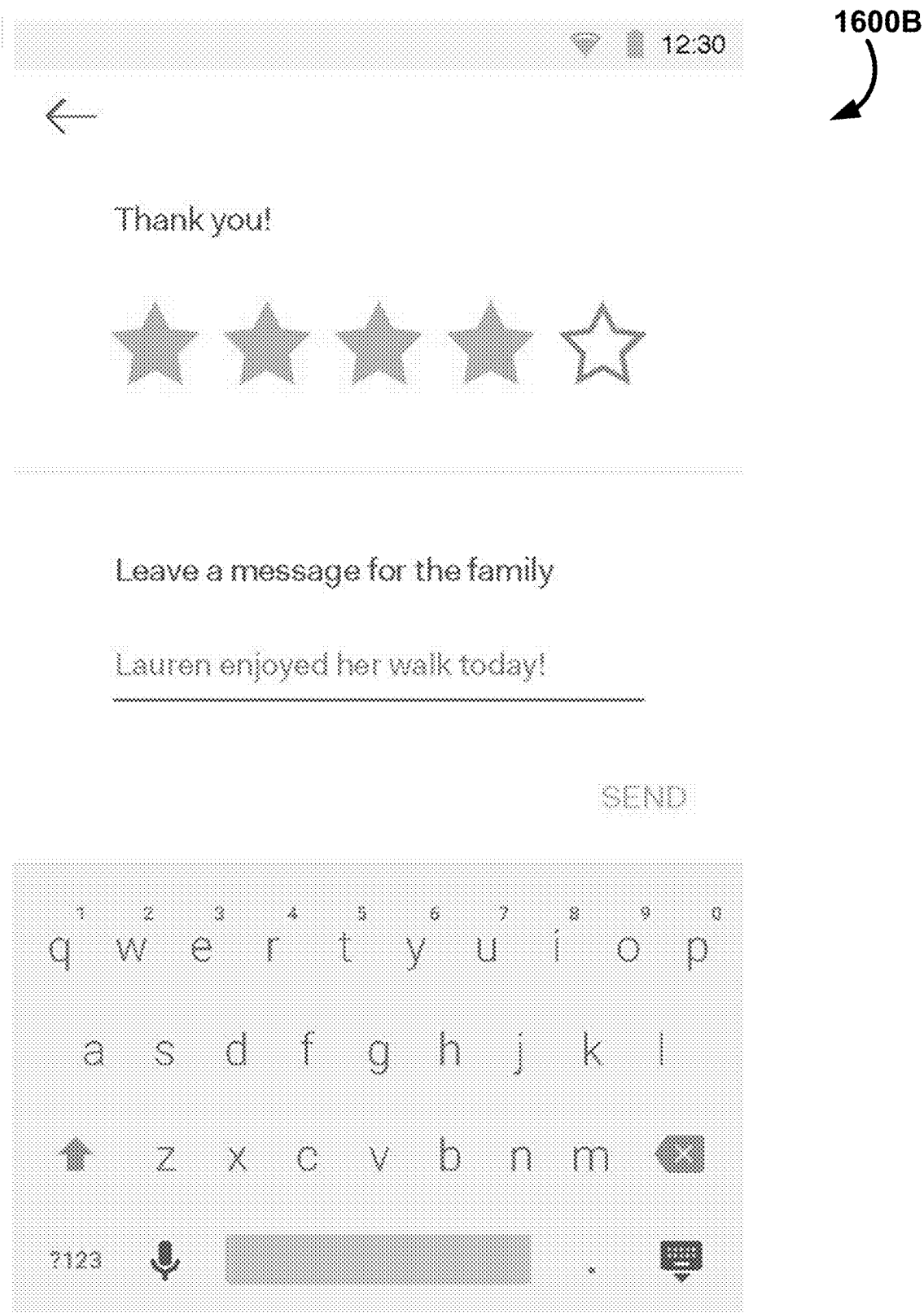

Each activity may include a toggle box for tracking the completion of any given task. Once all tasks have been completed, the provider also has the option to clock-out in order to render the appointment completed. Upon appointment completion, the provider may be asked to rate the appointment, as shown generally at 1600A in reference to FIG. 16A. The rating may be kept confidential from the recipient in order to facilitate honest feedback. This data, in conjunction with recipient ratings of the provider, are utilized to best match the recipient to the providers, and when necessary, alter the existing services being rendered to the recipient, as previously discussed. In addition to the rating, the provider may be given the opportunity to compose a message for the family and friends of the recipient. FIG. 16B illustrates a screenshot once the provider has input the review and a message for the family, shown generally at 1600B. This messaging, along with the ability to track appointment progression, gives the family significant peace of mind that is currently lacking among most traditionally provided services.

Figure 17:
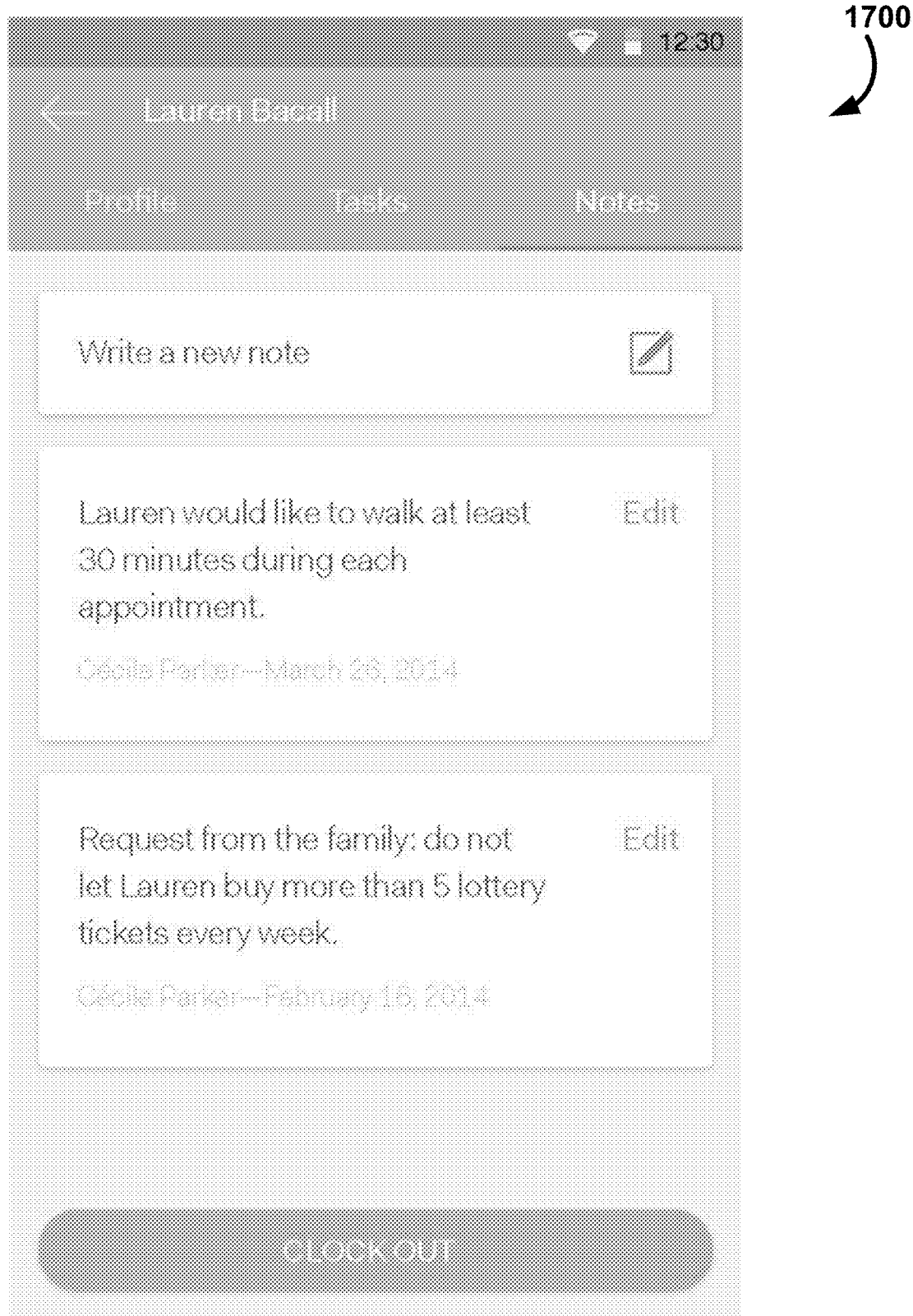
Figure 18:
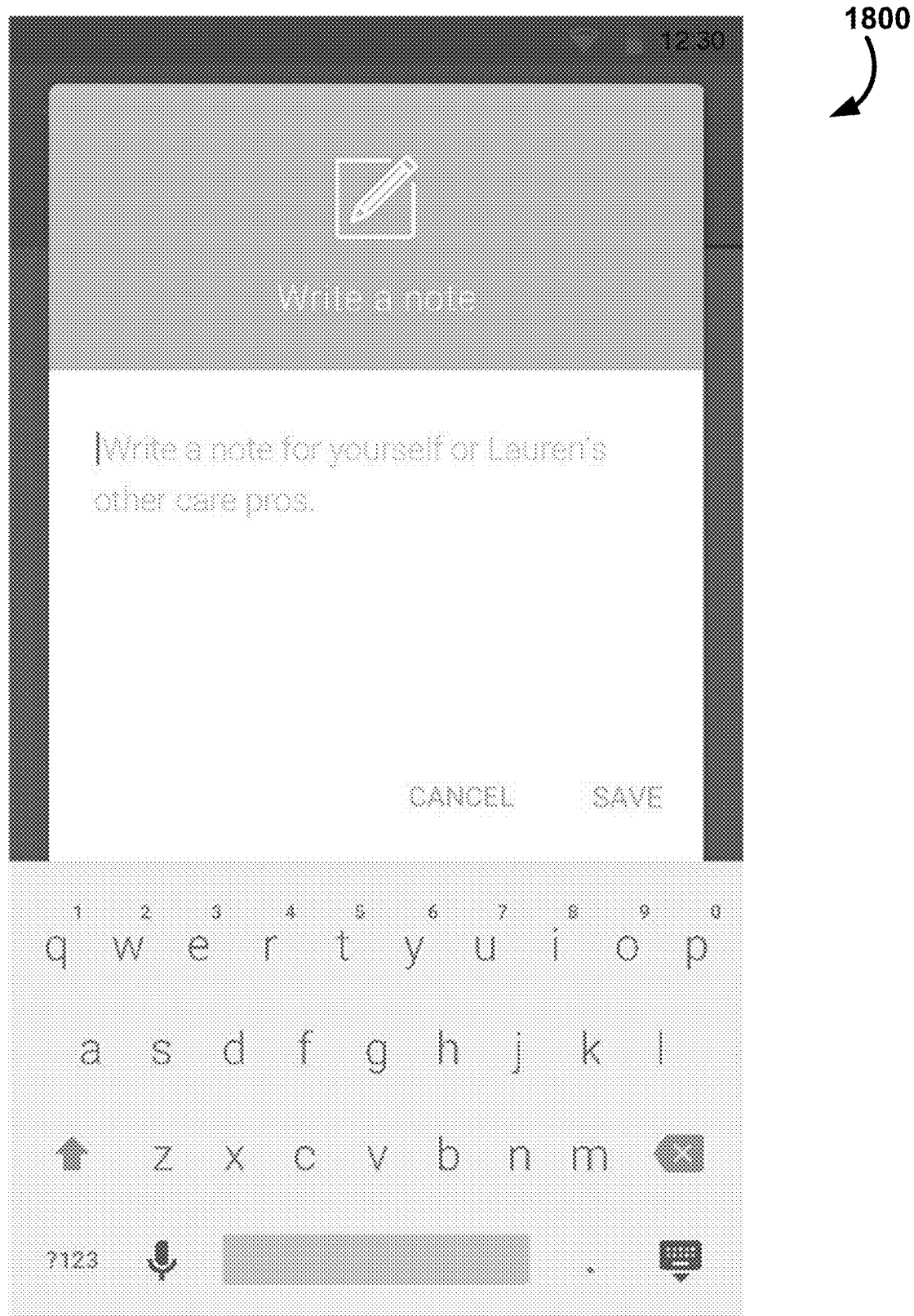

FIG. 17 provides an example screenshot of the notes portion of the recipient's file, shown generally at 1700. These notes may be compiled and edited by the provider at any time, and may be used to maintain reminders for the provider. As illustrated herein, the family of the giver recipient has requested the provider to limit the recipient's purchases of lottery tickets. Additionally, the provider has included a note about the type of activity the recipient has requested at the appointments. FIG. 18 provides a screenshot of an example where the provider has selected to draft a new note, shown generally at 1800. As previously mentioned, these notes may be exclusive to the provider, or may be shared among all care providers who visit the recipient.

Figure 19:
Figure 20:

FIG. 19 provides an example screenshot of the provider's client menu, shown generally at 1900. From this page, any of the clients/recipients may be selected, and their profile and care plan is displayed to the provider. For example, when the recipient's name or image is selected, the profile page is displayed, as generally shown at 2000 in reference to FIG. 20. The recipient profile includes their name, image, and a litany of personal information. The profile displayed is provided by way of example, and any of this information may be included in a recipient's profile. However, it should also be understood that a recipient's profile in some embodiments may include substantially more or less information, based upon the given needs of the system and providers or the preferences of the recipient.

In this example profile, the next appointment, address, age, gender, height, weight, preferred salutation, physical limitations, mental limitations, pets, smell sensitivity, preference to providers wearing shoes inside the home, current or previous profession, greatest accomplishment, best gift received, favorite holiday, most treasured memory, best feature, favorite person, perfect day, and friendship value are all displayed. In addition, a typical profile may also include information about family, favorite conversational topics, favorite foods, favorite activities, TV preference, compulsions, etc. which may be helpful in navigating the interactions between the provider and recipient.

Moving on, when the care plan menu is selected, a screen is displayed that illustrates the tasks associated with the recipient, recent notes, and the schedule for appointments, as seen generally at 2100 in reference to FIG. 21. This allows the provider to rapidly find an overview of the recipient's needs, and scheduled interactions.

Figure 22:
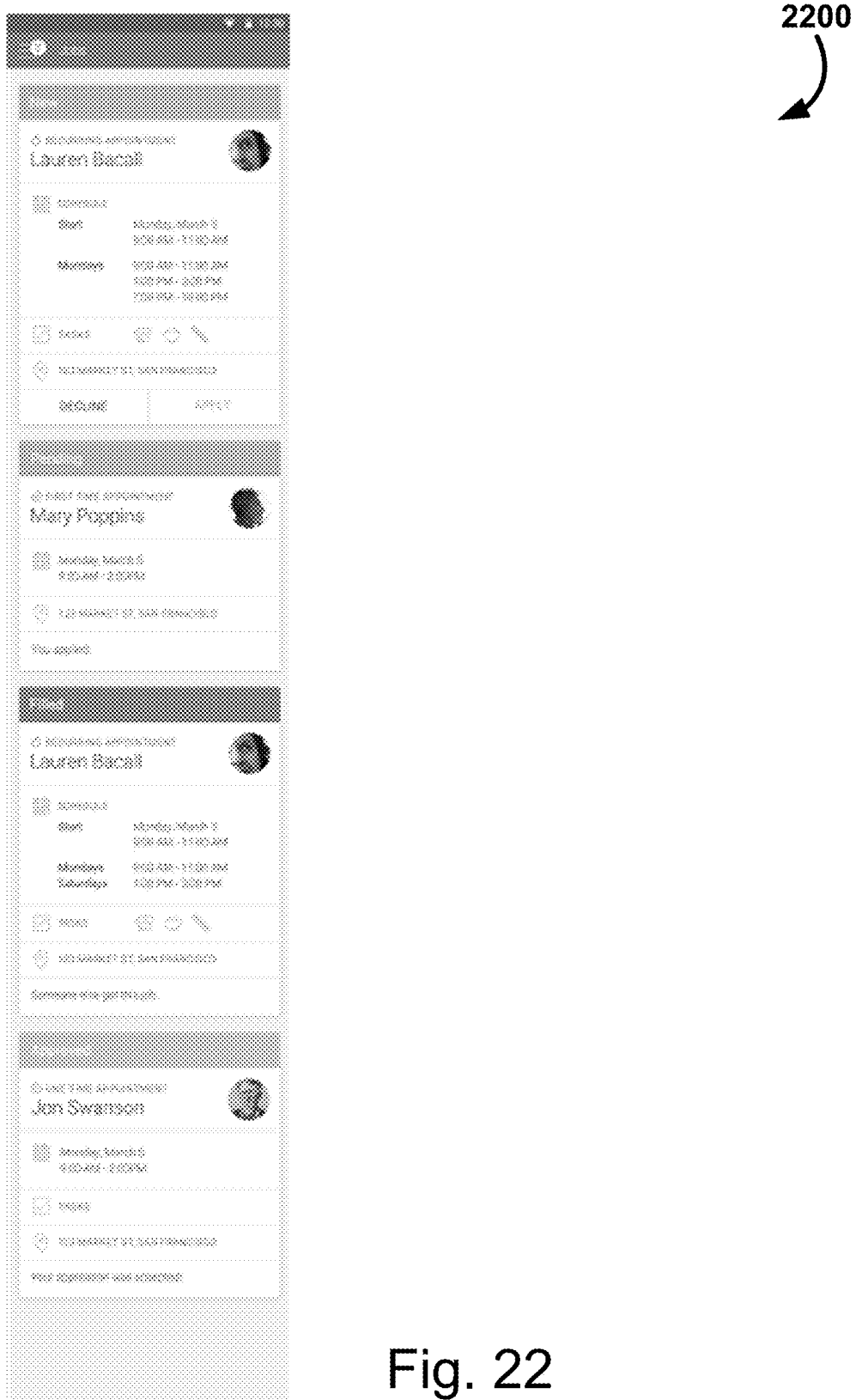

FIG. 22 illustrates an example screenshot of the jobs menu that may be selected form the provider's home screen, shown generally at 2200. As previously discussed, providers and recipients may be matched in a number of ways, depending upon system embodiment. In some cases, the system employs matching optimizations in order to pair recipients to providers; however, in other embodiments, a marketplace style exchange may be generated which allows providers to directly pursue a given opportunity. The presently illustrated example screenshot is one such embodiment of such a marketplace. Here new opportunities may be first presented to the provider based upon matching optimizations. In such embodiments, many providers are selected for the opportunity, and each is provided the option to pursue or decline the opportunity (as seen in the first listed job). Details regarding the recipient, time, tasks and location are given to the provider in order to ensure their decision is well informed.

If the provider decides to pursue the opportunity, then the status is changed from 'new' to 'pending' while the provider's information is forwarded to the recipient and/or the recipient's friends and family. Once the recipient and/or the recipient's friends and family have collected the information of several interested providers, they may select the providers that they think may be the best match.

From the provider's perspective, if the recipient chooses another provider, the job status will be changed from 'pending' to 'filled'. Alternatively, if they are accepted for the opportunity, the status updates to 'approved'. In this manner, the providers may be efficiently matched with recipients via a marketplace style exchange. As part of the application process, information may also be given to the recipient and/or the recipient's friends and family regarding provider's ratings, fit as determined by the optimization process, payment requirements, etc. Also, as mentioned, the provider's profile is included when they pursue an opportunity. .

Figure 23:
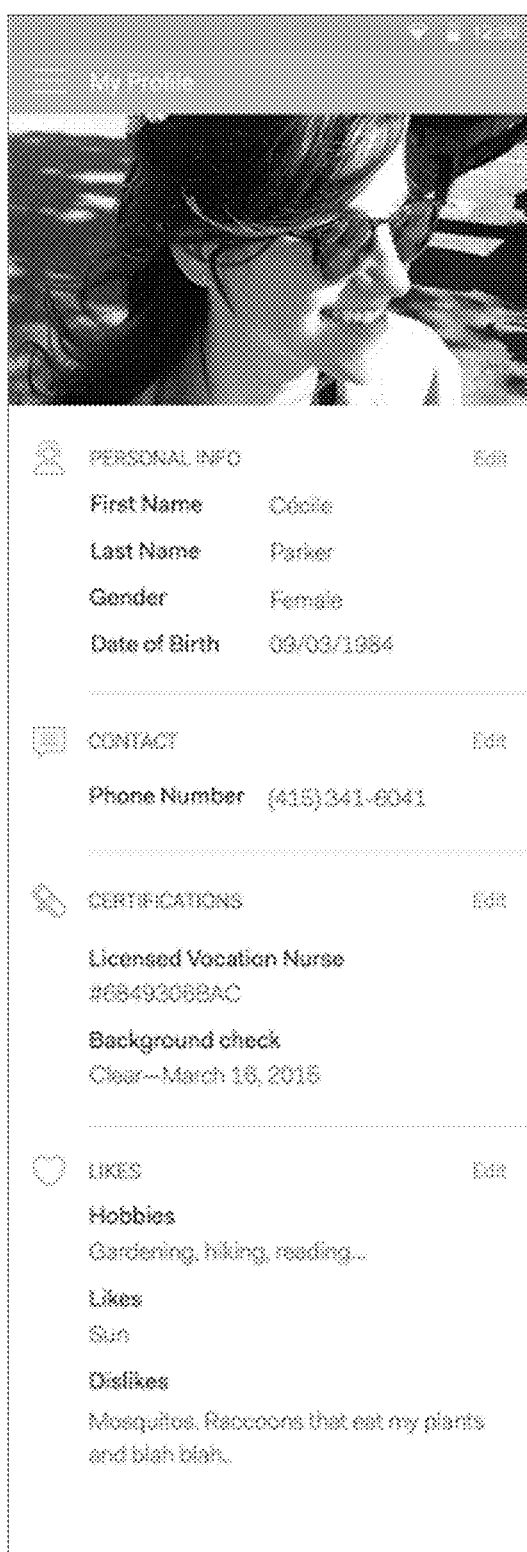

FIG. 23 illustrates, at 2300, an example screenshot of such a provider profile. Much like the recipient profile, the provider's name and image are included, as well as personal information such as birthday, contract information, certifications, and personal preferences (hobbies, likes and dislikes). Also included in some profiles are professional history, languages spoken, and other relevant information. Again, this profile information may be employed by the matching optimization to ensure appropriate providers are matched with any given recipient.

Moving on to the recipient's side of things, the presently disclosed systems include a device that is deployed within the recipient's home that provides information regarding upcoming appointments. Generally this device is locked in order to provide resilient and limited functionality in order to limit the possibility of user error. This is particularly important for recipients who are elderly, unfamiliar with technology, or mentally handicapped. However, it may also be envisioned, that for recipients who are technologically savvy, the device may include an existing tablet, smartphone or laptop with an application running on it. Such devices may have enhanced functionality, as has already been discussed.

Figure 24:
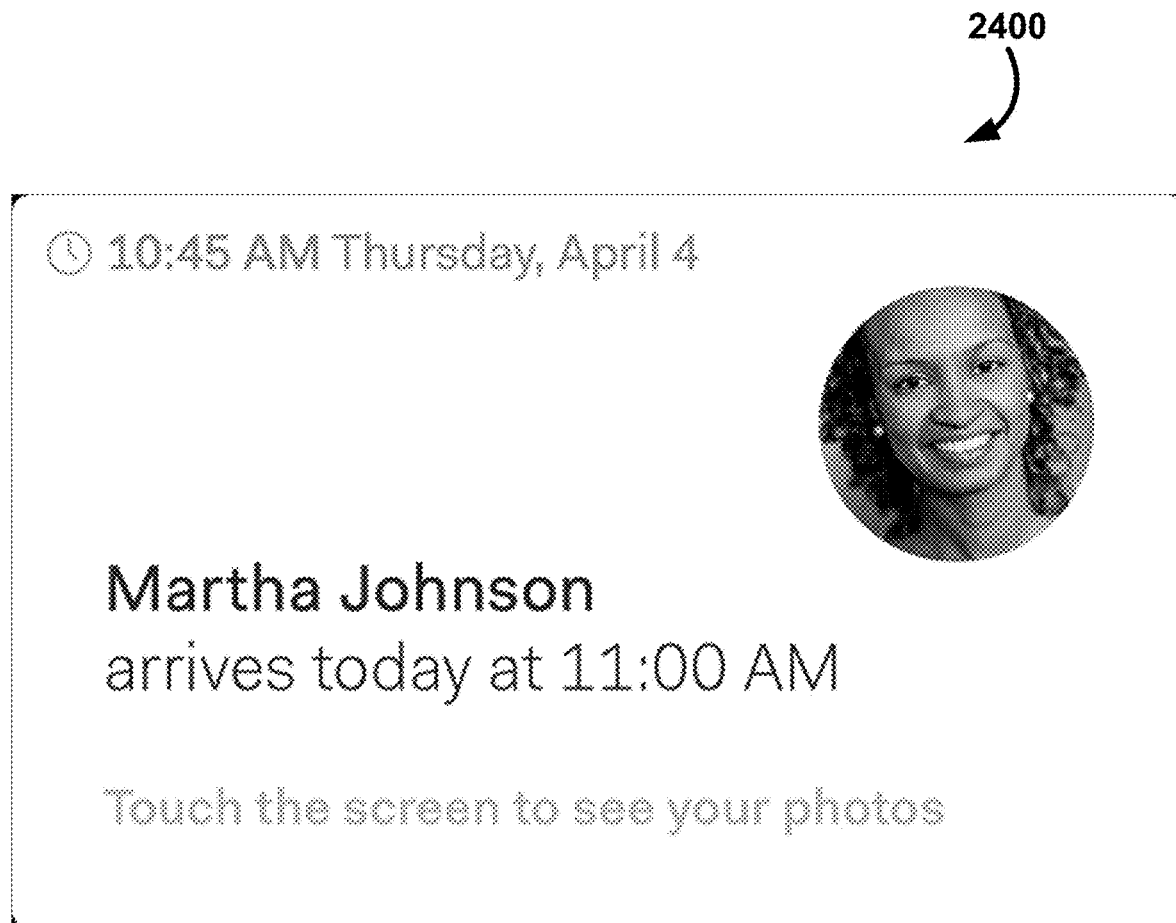

FIG. 24 illustrates an example screenshot of one such embodiment where information regarding an upcoming appointment is displayed to the recipient, shown generally at 2400. Here the current date and time are displayed, along with the time of the appointment, and name and image of the provider. In this embodiment, the device may also have photograph loaded onto it, and may provide the option for the recipient to view their personal photos.

Figure 25A:
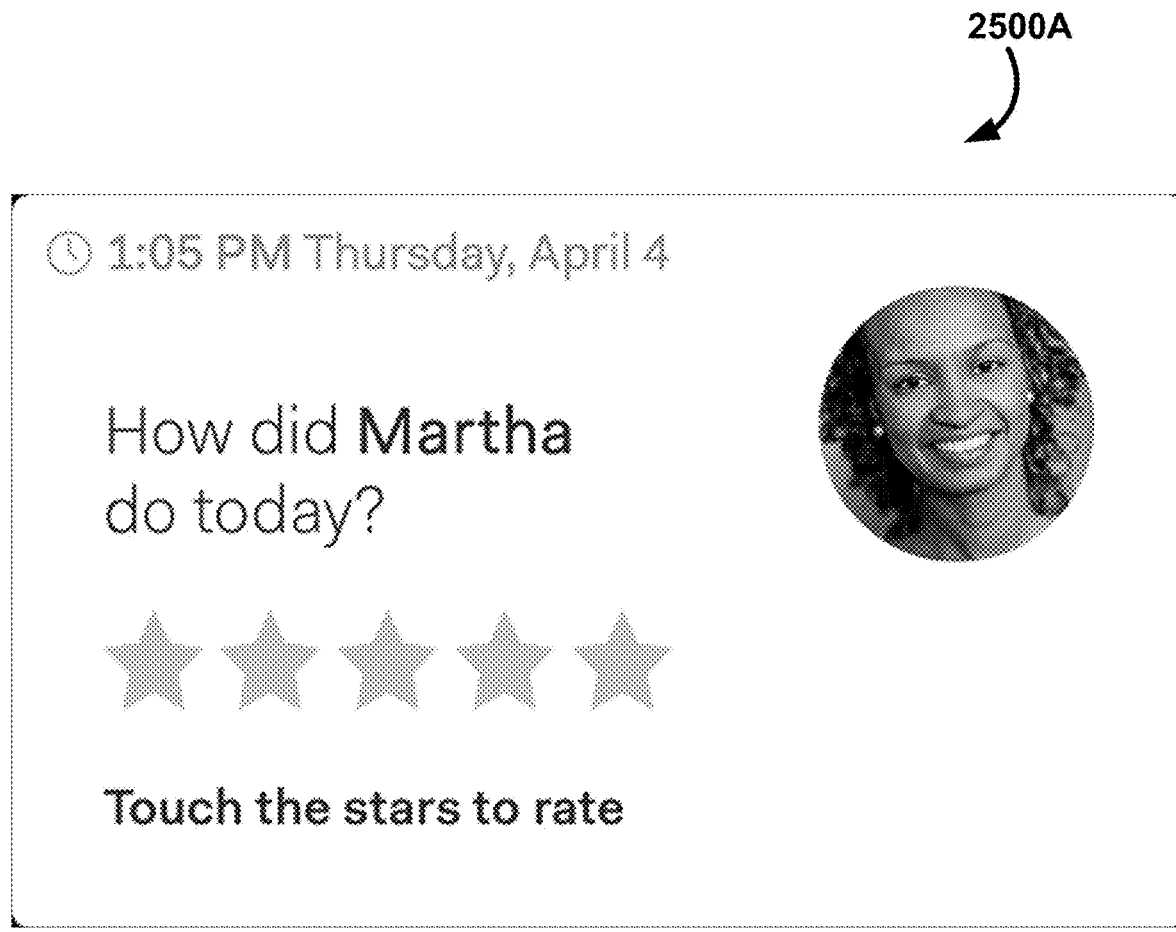
Figure 25B:
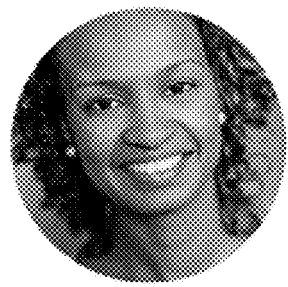
Figure 25B:
Figure 25C:
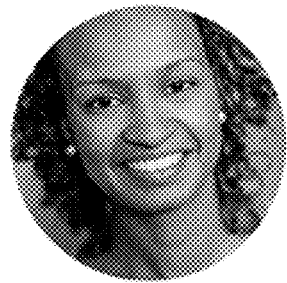

Upon completion of the appointment, as indicated by the provider clocking out of the appointment via their own device, the recipient's device may request feedback regarding the provider, as shown at 2500A of FIG. 25A. Again, this feedback may be confidential in order to promote honest answers, and is utilized in the matching optimization and care adjustment processes. FIG. 25B illustrates, at 2500B, once the recipient has selected a rating for the provider, and FIG. 25C illustrates, at 2500C that the feedback has been successfully submitted.

Figure 26A:
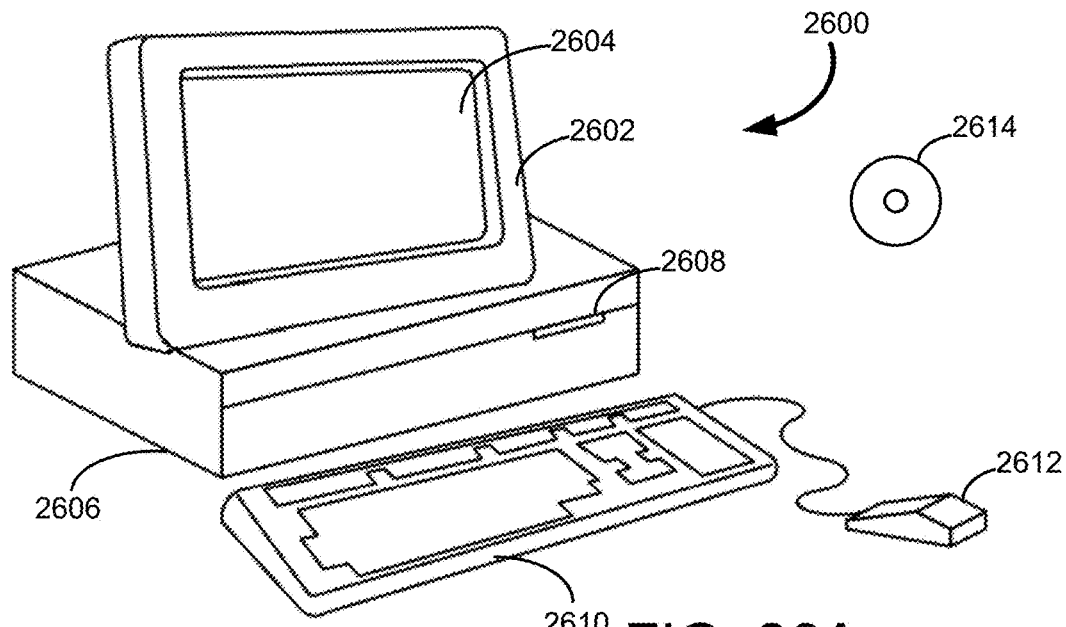
FIGS. 26A and 26B are example computer systems capable of implementing the system for remote care management, in accordance with some embodiments.
Figure 26B:
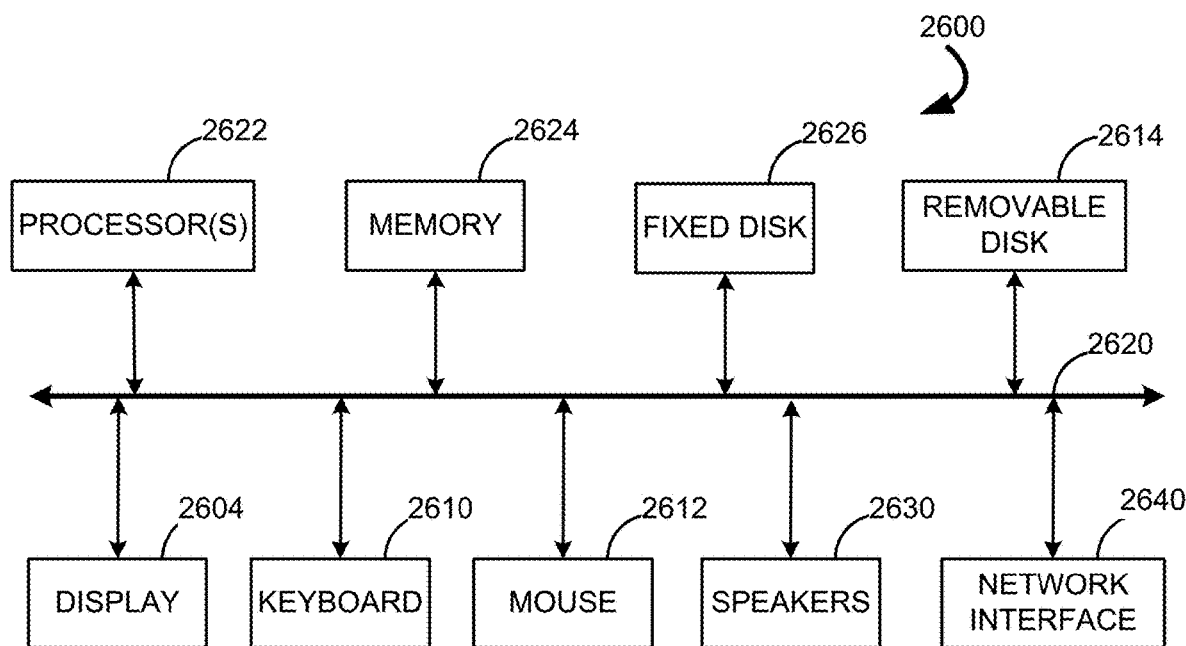

Lastly, FIGS. 26A and 26B illustrate a Computer System 2600, which is suitable for implementing embodiments of the present invention. FIG. 26A shows one possible physical form of the Computer System 2600. Of course, the Computer System 2600 may have many physical forms ranging from a printed circuit board, an integrated circuit, and a small handheld device up to a huge super computer. Computer system 2600 may include a Monitor 2602, a Display 2604, a Housing 2606, a Disk Drive 2608, a Keyboard 2610, and a Mouse 2612. Disk 2614 is a computer-readable medium used to transfer data to and from Computer System 2600.

FIG. 26B is an example of a block diagram for Computer System 2600. Attached to System Bus 2620 are a wide variety of subsystems. Processor(s) 2622 (also referred to as central processing units, or CPUs) are coupled to storage devices, including Memory 2624. Memory 2624 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 2626 may also be coupled bi-directionally to the Processor 2622; it provides additional data storage capacity and may also include any of the computer-readable media described below. Fixed Disk 2626 may be used to store programs, data, and the like and is typically a secondary storage medium (such as a hard disk) that is slower than primary storage. It will be appreciated that the information retained within Fixed Disk 2626 may, in appropriate cases, be incorporated in standard fashion as virtual memory in Memory 2624. Removable Disk 2614 may take the form of any of the computer-readable media described below.

Processor 2622 is also coupled to a variety of input/output devices, such as Display 2604, Keyboard 2610, Mouse 2612 and Speakers 2630. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 2622 optionally may be coupled to another computer or telecommunications network using Network Interface 2640. With such a Network Interface 2640, it is contemplated that the Processor 2622 might receive information from the network, or might output information to the network in the course of performing the above-described care management. Furthermore, method embodiments of the present invention may execute solely upon Processor 2622 or may execute over a network such as the Internet in conjunction with a remote CPU that shares a portion of the processing.

In sum, the present invention provides systems and methods for the management of remote care delivery. The advantages of such a system include the ability to improve the efficiency of care delivery through better routing and scheduling of providers, better matching of providers to recipients, and enhanced transparency that provides family and friends of the recipient peace of mind.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computerized system for monitoring a recipient of care, the system comprising:
 a confirmation engine on a server configured to receive confirmation from a mobile device that a provider of care has completed the care of the recipient;

messaging system on the mobile device configured to receive a message regarding the care delivery from the provider;

an application interface configured to convey the confirmation and message to friends and family of the recipient; and a security module comprising at least one server configured to:

collect a motion detection feed of the recipient from the recipient's location using at least one non-camera motion sensor to maintain privacy of the recipient;

determine when the recipient is motionless above one threshold selected from of a plurality of thresholds of time, wherein the one threshold is selected based upon the location;

activate a video recording device to collect video in the recipients location responsive to the determining; and transmit the video to at least one operator in real time.

2. The system of claim 1, wherein the security module cross references time and location of the provider against the confirmation to determine if there is a discrepancy.

3. The system of claim 1, wherein the collected feed includes at least one of a video feed, an audio feed, an emergency signal, and a message from the provider.

4. The system of claim 3, wherein the feed is collected when the provider is at the recipient's location.

5. The system of claim 3, wherein the security module is further configured to analyze the feeds for trigger events, wherein a trigger event includes at least one of an audible call for help, unexpected movement, and lack of movement for a configured period of time.

6. The system of claim 5, wherein the security module is further configured to relay the feed to a human operator if a trigger event is detected.

7. The system of claim 6, further comprising a dispatch module to dispatch any of a provider or emergency responder if directed by the human operator.

8. The system of claim 7, further comprising a reporting module configured to report out findings resulting from the dispatch.

9. The system of claim 1, wherein the messaging system if configured to provide bidirectional communication between the provider and the recipient's friends and family.

10. A computerized method for monitoring a recipient of care, the system comprising:

receiving confirmation at a server from a mobile device that a provider of care has completed the care of the recipient;

receiving a message on the mobile device regarding the care delivery from the provider;

conveying the confirmation and message to friends and family of the recipient;

collecting a motion detection feed of the recipient from the recipient's location using at least one non-camera motion sensor to maintain privacy of the recipient;

determining when the recipient is motionless above one threshold selected from of a plurality of thresholds of time, wherein the one threshold is selected based upon the location;

activating a video recording device to collect video in the recipient's location responsive to the determining; and transmitting the video to at least one operator in real time.

11. The method of claim 10, wherein the identifying lapses of care and emergencies includes cross referencing time and location of the provider against the confirmation to determine if there is a discrepancy.

12. The method of claim 10, wherein the collected feed includes at least one of a video feed, an audio feed, an emergency signal, and a message from the provider.

13. The method of claim 12, wherein the feed is collected when the provider is at the recipient's location.

14. The method of claim 12, further comprising analyzing the feeds for trigger events, wherein a trigger event includes at least one of an audible call for help, unexpected movement, and lack of movement for a configured period of time.

15. The method of claim 14, further comprising relaying the feed to a human operator if a trigger event is detected.

16. The method of claim 15, further comprising dispatching any of a provider or emergency responder if directed by the human operator.

17. The method of claim 16, further comprising reporting out findings resulting from the dispatch.

18. The method of claim 10, further comprising providing bidirectional communication between the provider and the recipient's friends and family.

* * * * *